United States Patent
Haseeb et al.

(10) Patent No.: US 11,309,061 B1
(45) Date of Patent: Apr. 19, 2022

(54) SYSTEMS AND METHODS FOR PEPTIDE IDENTIFICATION

(71) Applicants: Muhammad Haseeb, Miami, FL (US); Fahad Saeed, Miami, FL (US)

(72) Inventors: Muhammad Haseeb, Miami, FL (US); Fahad Saeed, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/366,618

(22) Filed: Jul. 2, 2021

(51) Int. Cl.
  G16B 35/10 (2019.01)
  G16B 50/30 (2019.01)
  G06F 9/50 (2006.01)
  G16B 40/10 (2019.01)

(52) U.S. Cl.
  CPC ............ *G16B 35/10* (2019.02); *G06F 9/505* (2013.01); *G06F 9/5016* (2013.01); *G16B 40/10* (2019.02); *G16B 50/30* (2019.02)

(58) Field of Classification Search
  CPC ........ G16B 35/10; G16B 50/30; G16B 40/10; G06F 9/5016; G06F 9/505
  See application file for complete search history.

(56) References Cited

U.S. PATENT DOCUMENTS

| | | | | |
|---|---|---|---|---|
| 9,354,236 B2 * | 5/2016 | Albar Ramirez | ...... | G16B 20/00 |
| 2004/0044481 A1 * | 3/2004 | Halpern | ................ | G16B 50/00 |
| | | | | 702/19 |
| 2005/0209833 A1 * | 9/2005 | Bishop | .................... | H04L 67/22 |
| | | | | 703/2 |
| 2013/0117326 A1 * | 5/2013 | De Smet | ............... | G06F 9/4488 |
| | | | | 707/798 |
| 2014/0143789 A1 * | 5/2014 | Nadathur | ................ | G06F 9/505 |
| | | | | 718/105 |
| 2020/0243164 A1 * | 7/2020 | Qiao | ...................... | G16B 25/10 |

(Continued)

OTHER PUBLICATIONS

Kulkarni et al. "A scalable parallel approach for peptide identification from large-scale mass spectrometry data." 2009 International Conference on Parallel Processing Workshops. IEEE, pp. 423-430 (Year: 2009).*

(Continued)

*Primary Examiner* — Meng Ai T An
*Assistant Examiner* — Willy W Huaracha
(74) *Attorney, Agent, or Firm* — Saliwanchik, Lloyd & Eisenschenk

(57) ABSTRACT

Provided are parallel computational methods and their implementation on memory-distributed architectures for a peptide identification tool, called HiCOPS, that enables more than 100-fold improvement in speed over existing HPC proteome database search tools. HiCOPS empowers the supercomputing database search for comprehensive identification of peptides and all their modified forms within a reasonable timeframe. Searching Gigabytes of experimental mass spectrometry data against Terabytes of databases demonstrates peptide identification in minutes compared to days or weeks, providing multiple orders of magnitude improvements in processing times. Also provided is a theoretical framework for a novel overhead-avoiding strategy, resulting in superior performance evaluation results for key metrics including execution time, CPU utilization, and I/O efficiency.

16 Claims, 19 Drawing Sheets

(56) References Cited

U.S. PATENT DOCUMENTS

2020/0303034 A1* 9/2020 Park .................. G16B 35/20
2020/0381231 A1* 12/2020 Bailey ............... H01J 49/0036
2021/0041454 A1* 2/2021 Tsou .................. G16B 40/20
2021/0215707 A1* 7/2021 Marcotte ............ G16B 50/00

OTHER PUBLICATIONS

Haseeb et al. "LBE: A computational load balancing algorithm for speeding up parallel peptide search in mass-spectrometry based proteomics." 2019 IEEE International Parallel and Distributed Processing Symposium Workshops (IPDPSW). IEEE, pp. 191-198 (Year: 2019).*

Haseeb et al. "HiCOPS: High Performance Computing Framework for Tera-Scale Database Search of Mass Spectrometry based Omics Data." arXiv preprint arXiv:2102.02286, pp. 1-37. (Year: 2021).*

* cited by examiner

SYSTEMS AND METHODS FOR PEPTIDE IDENTIFICATION

GOVERNMENT SUPPORT

This invention was made with government support under NSF CAREER OAC-1925960 awarded by National Science Foundation. The government has certain rights in the invention.

BACKGROUND

Identification of peptides through database peptide search technique requires searching several gigabytes of data against several hundred gigabytes to a few terabytes of database using resource (e.g., computational and memory) intensive algorithms. Known high-performance computing (HPC) techniques for database peptide search have been designed as serial methods and thus do not scale with problem size.

Database-search algorithms, that deduce peptides from mass spectrometry (MS) data, have tried to improve the computational efficiency to accomplish larger and more complex systems biology studies. Existing serial, and high-performance computing (HPC) search engines, otherwise highly successful, are known to exhibit poor-scalability with increasing size of theoretical search-space needed for increased complexity of modern non-model, multi-species MS-based omics analysis. Consequently, the bottleneck for computational techniques is the communication costs of moving the data between a hierarchy of memory, or processing units, and not the arithmetic operations. This post-Moore change in architecture and demands of modern systems biology experiments have dampened the overall effectiveness of the existing HPC workflows.

BRIEF SUMMARY

Embodiments of the subject invention provide systems for rapid and efficient peptide identification from large-scale mass spectrometry data through high performance computing database peptide search. The system can comprise a symmetric multiprocessor supercomputer comprising a plurality of processors and shared resources, the shared resources comprising a shared memory storage in operable communication with the plurality of processors; and at least one (non-transitory) machine-readable medium in operable communication with the plurality of processors, the at least one machine-readable medium having instructions stored thereon that, when executed by one or more of the plurality of processors, perform the following supersteps: (a) providing a plurality of load balanced, indexed, peptide database partitions (PDB) from a peptide database; (b) providing a plurality of spectra, each spectra comprising a batch of pre-processed mass spectrometry data from a mass spectrometry data set; (c) completing a partial database peptide search of the plurality of spectra against the plurality of PDBs to produce a plurality of intermediate results; and (d) assembling, deserializing, and synchronizing the plurality of intermediate results to form a complete result, and writing the complete result to a file system, thus providing the rapid and efficient peptide identification from large-scale mass spectrometry data.

In an embodiment, the superstep (a) may comprise peptide database clustering based on a Mod Distance (Δm). The Mod Distance (Δm) may be given as:

$$\Delta m(x, y) = 2 - \frac{a}{\max(len(x), len(y))}$$

for a pair of peptide database entries (x, y), where the sum of unedited letters from both sequence termini is (a).

In certain embodiments, each of the plurality of processors may have a main memory locally connected, each of the plurality of spectra provided in superstep (b) having a size selected to fit within the main memory on one of the plurality of processors.

In an embodiment, the partial database peptide search may comprise the following steps:

(R) loading the plurality of spectra into a plurality of forward queues (qf) in the shared memory storage;

(I) reading the spectra from each respective forward queue in the plurality of forward queues, recycling the forward queue as a return queue (qr), searching the spectra against the plurality of PDB to produce the plurality of intermediate results, and writing the plurality of intermediate results to a plurality of intermediate queues (qk) in the shared memory storage; and (K) reading the intermediate results from each respective intermediate queue in the plurality of intermediate queues, recycling each intermediate queue as an intermediate return queue (qk'), serializing the plurality of intermediate results and writing the plurality of intermediate results to the shared memory storage.

In an embodiment, the superstep (c) may comprise actively allocating shared resources across steps (R), (I), and (K) to optimize performance in a multi-threaded, multi-core, shared memory, parallel process, producer-consumer pipeline. The system can comprise measurable performance parameters, the performance parameters comprising: shared memory per node (k), NUMA nodes per node (u), cores per NUMA node (cu), number of sockets per node (s), cores per socket (cs), estimated or actual total size of database (D), total number of system nodes (P), number of MPI tasks per node (tn), number of parallel cores per MPI task (tc), and MPI task binding level (tbl); and superstep (c) comprising determining allocation of shared resources based on one or more of the performance parameters.

An embodiment provides the superstep (d) comprising a first parallel sub-task comprising de-serialization and assembly of the plurality of intermediate results, and a second parallel sub-task comprising data smoothing and application of a significance test to compute e-Values. The symmetric multiprocessor supercomputer can comprise processing cores allocated to tasks, the system comprising a step of iteratively reducing the cores per task while increasing the number of tasks until the PDB size per task reaches the user-defined threshold, which may be set according to the available RAM per node.

Embodiments also provide methods for rapid and efficient peptide identification from large-scale mass spectrometry data through high performance computing database peptide search. The method can comprise providing a symmetric multiprocessor supercomputer comprising a plurality of processors and shared resources, the shared resources comprising a shared memory storage in operable communication with the plurality of processors, and at least one machine-readable medium in operable communication with the plurality of processors; and performing the following supersteps:

(a) providing a plurality of load balanced, indexed, peptide database partitions (PDB) from a peptide database;

(b) providing a plurality of spectra, each spectra comprising a batch of pre-processed mass spectrometry data from a mass spectrometry data set;
(c) completing a partial database peptide search of the plurality of spectra against the plurality of PDBs to produce a plurality of intermediate results; and
(d) assembling, deserializing, and synchronizing the plurality of intermediate results to form a complete result, and writing the complete result to a file system, thus providing the rapid and efficient peptide identification from large-scale mass spectrometry data.

Embodiments provide the superstep (a) comprising peptide database clustering based on a Mod Distance (Δm), the Mod Distance (Δm) is given as:

$$\Delta m(x, y) = 2 - \frac{a}{\max(len(x), len(y))}$$

for a pair of peptide database entries (x, y), where the sum of unedited letters from both sequence termini is (a).

In an embodiment, each of the plurality of processors can have a main memory locally connected, and each of the plurality of spectra provided in superstep (b) can have a size selected to fit within the main memory on one of the plurality of processors. The partial database peptide search can comprise the following steps:

(R) loading the plurality of spectra into a plurality of forward queues (qf) in the shared memory storage;

(I) reading the spectra from each respective forward queue in the plurality of forward queues, recycling the forward queue as a return queue (qr), searching the spectra against the plurality of PDB to produce the plurality of intermediate results, and writing the plurality of intermediate results to a plurality of intermediate queues (qk) in the shared memory storage; and (K) reading the intermediate results from each respective intermediate queue in the plurality of intermediate queues, recycling each intermediate queue as an intermediate return queue (qk'), serializing the plurality of intermediate results and writing the plurality of intermediate results to the shared memory storage.

Embodiments provide the superstep (c) comprising actively allocating shared resources across steps (R), (I), and (K) to optimize performance in a multi-threaded, multi-core, shared memory, parallel process, producer-consumer pipeline. The system can comprise measurable performance parameters, the performance parameters comprising: shared memory per node (k), NUMA nodes per node (u), cores per NUMA node (cu), number of sockets per node (s), cores per socket (cs), estimated or actual total size of database (D), total number of system nodes (P), number of MPI tasks per node (tn), number of parallel cores per MPI task (tc), and MPI task binding level (tbl); and superstep (c) comprising determining allocation of shared resources based on one or more of the performance parameters.

The superstep (d) can comprise a first parallel sub-task comprising de-serialization and assembly of the plurality of intermediate results, and a second parallel sub-task comprising data smoothing and application of a significance test to compute e-Values.

In an embodiment, a system for rapid and efficient peptide identification from large-scale mass spectrometry data through high performance computing database peptide search can comprise a symmetric multiprocessor supercomputer comprising a plurality of processors and shared resources, the shared resources comprising a shared memory storage in operable communication with the plurality of processors and at least one machine-readable medium in operable communication with the plurality of processors, the at least one machine-readable medium having instructions stored thereon that, when executed by one or more of the plurality of processors, perform the following supersteps:

(a) providing a plurality of load balanced, indexed, peptide database partitions (PDB) from a peptide database;
(b) providing a plurality of spectra, each spectra comprising a batch of pre-processed mass spectrometry data from a mass spectrometry data set;
(c) completing a partial database peptide search of the plurality of spectra against the plurality of PDBs to produce a plurality of intermediate results; and
(d) assembling, deserializing, and synchronizing the plurality of intermediate results to form a complete result, and writing the complete result to a file system, thus providing the rapid and efficient peptide identification from large-scale mass spectrometry data;

the superstep (a) comprising peptide database clustering based on a Mod Distance (Δm), given as:

$$\Delta m(x, y) = 2 - \frac{a}{\max(len(x), len(y))}$$

for a pair of peptide database entries (x, y), where the sum of unedited letters from both sequence termini is (a); each of the plurality of processors having a main memory locally connected, and each of the plurality of spectra provided in superstep (b) having a size selected to fit within the main memory on one of the plurality of processors; the partial database peptide search comprising the following steps:

(R) loading the plurality of spectra into a plurality of forward queues (qf) in the shared memory storage;

(I) reading the spectra from each respective forward queue in the plurality of forward queues, recycling the forward queue as a return queue (qr), searching the spectra against the plurality of PDB to produce the plurality of intermediate results, and writing the plurality of intermediate results to a plurality of intermediate queues (qk) in the shared memory storage; and (K) reading the intermediate results from each respective intermediate queue in the plurality of intermediate queues, recycling each intermediate queue as an intermediate return queue (qk'), serializing the plurality of intermediate results and writing the plurality of intermediate results to the shared memory storage, and the superstep (c) comprising actively allocating shared resources across steps (R), (I), and (K) to optimize performance in a multi-threaded, multi-core, shared memory, parallel process, producer-consumer pipeline.

In an embodiment, the system can comprise measurable performance parameters, the performance parameters comprising: shared memory per node (k); NUMA nodes per node (u); cores per NUMA node (cu; number of sockets per node (s); cores per socket (cs); estimated or actual total size of database (D); total number of system nodes (P); number of MPI tasks per node (tn); number of parallel cores per MPI task (tc); and MPI task binding level (tbl). Superstep (c) can comprise determining allocation of shared resources based on one or more of the performance parameters. The superstep (d) can comprise a first parallel sub-task comprising de-serialization and assembly of the plurality of intermediate results, and a second parallel sub-task comprising data smoothing and application of a significance test to compute e-Values. The symmetric multiprocessor supercomputer can comprise processing cores allocated to tasks, the system comprising a step of iteratively reducing the cores per task while increasing the number of tasks until the PDB size per task reaches a defined threshold, the threshold being chosen to optimize system performance of the symmetric multiprocessor supercomputer.

DETAILED DESCRIPTION

Figure 1:
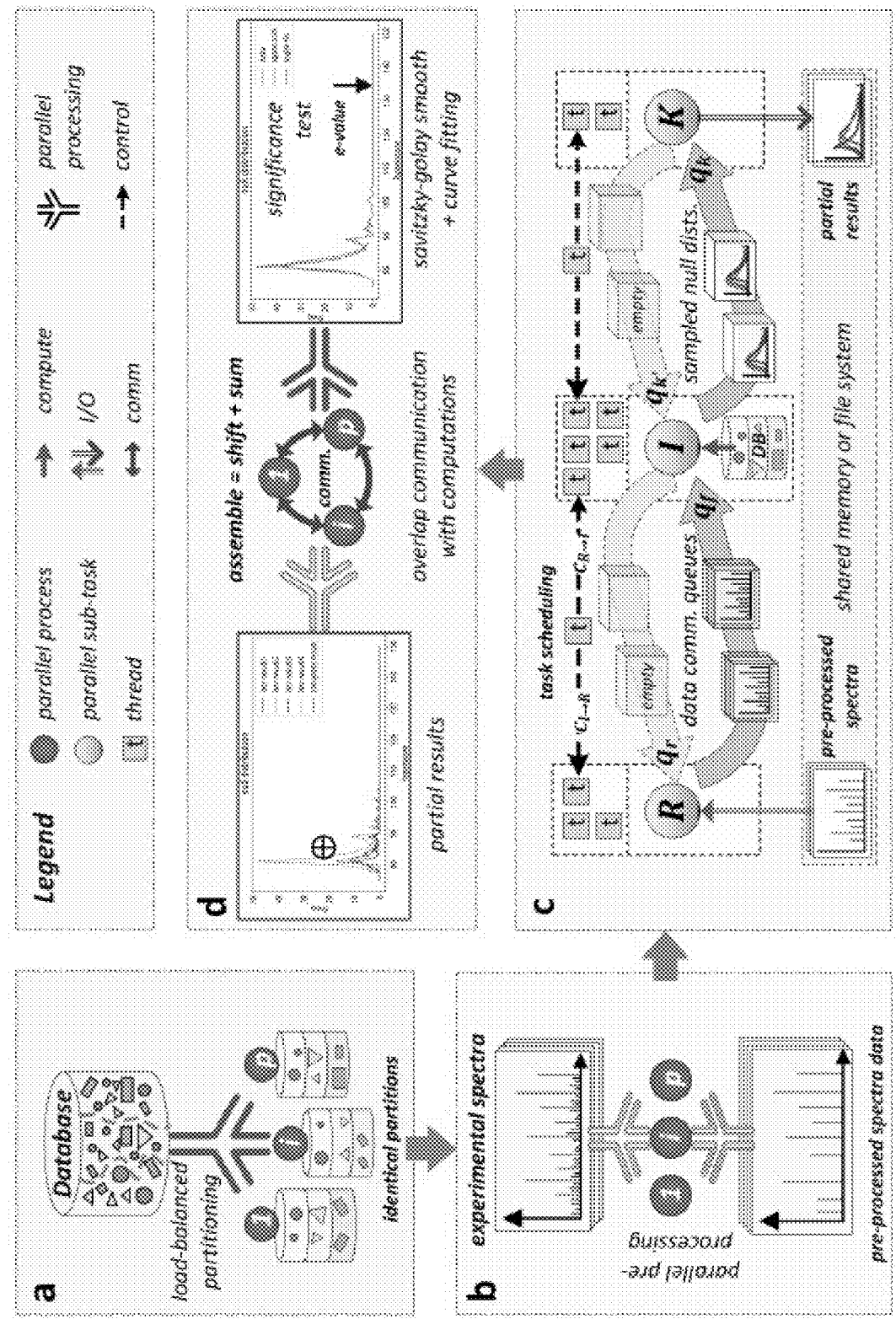
FIG. 1 is a schematic diagram representing a high-performance computing database peptide search process, according to an embodiment of the subject invention.

Embodiments of the subject invention provide novel distributed design strategies for accelerating the database peptide search workflows in high-performance computing (HPC) environments. Systems of embodiments of the subject invention can be referred to as "HiCOPS" throughout this disclosure. Embodiments are based on the Single Program Multiple Data (SPMD) bulk synchronous parallel (BSP) computational model and may build a task graph using four asynchronous parallel supersteps. A runtime cost model may be applied for performance analysis and optimizations. Experimental results show more than 100× improvement in speed over several existing shared-memory and distributed-memory methods. HiCOPS exhibits about 70-80% strong-scale efficiency for up to 72 parallel nodes (1728 cores) of the National Science Foundation's (NSF) Extreme Science and Engineering Discovery Environment (XSEDE) Comet cluster operated by the San Diego Supercomputing Center (SDSC). The results further show application in extremely large-scale experiments by showing that embodiments may search several gigabytes of data against terabyte level databases in few minutes compared to 35.5 days required by MSFragger (Kong et al., A. I., 2017, MSFragger: ultrafast and comprehensive peptide identification in mass spectrometrybased proteomics, Nature Methods, 14(5), 513-520; which is hereby incorporated herein by reference in its entirety), a widely used tool. A comprehensive performance evaluation revealed desirable results for several metrics including load balance, communication and I/O overheads, task scheduling and CPU utilization.

Embodiments provide a novel distributed design strategy, called HiCOPS, for accelerating the database peptide search workflows in HPC environments such as XSEDE and National Energy Research and Scientific Computing Center (NERSC) Cori supercomputers.

In extremely large-scale experiments, embodiments have been shown to search several gigabytes of experimental data against terabyte level databases in few minutes compared to 35.5 days required by MSFragger (a widely used search tool). Comprehensive performance evaluation revealed optimal results for several metrics including load balance (<10%), communication and I/O overheads (<10%), task scheduling (<5%) and CPU utilization (super linear for large experiments).

Embodiments can easily incorporate several existing serial algorithms and workflows for acceleration in HPC environments. Embodiments may implement parallel versions of many algorithms and data structures that can serve as building blocks for implementation of novel algorithms on top of a parallel core design.

The computational model employed in certain embodiments is a Single Program Multiple Data (SPMD) Bulk Synchronous Parallel (BSP) model where a set of processes execute (e.g., K) supersteps in asynchronous parallel fashion and synchronize between supersteps.

Embodiments may construct the parallel database peptide search algorithmic workflow (task-graph) using four supersteps:

1. In the first superstep, the massive model-spectra database is partitioned across parallel processes in a load balanced fashion (data parallel).

2. In the second superstep, the experimental data are divided into batches and pre-processed if required (data parallel).

3. In the third superstep, the parallel processes search batches of pre-processed experimental data against their partial databases, producing intermediate results (hybrid task and data parallel).

4. In the final superstep, the intermediate results are assembled into complete or global results and the statistical significance scores are computed (hybrid task and data parallel).

A runtime cost model for a superstep may count the time for any superstep as the maximum time that a process spends to complete that superstep in cases where the computational model is based on the SPMD parallel design.

1. Data Parallel supersteps:

$$Tj=\max(Tj,1,Tj,2,\ldots,Tj,p)$$

where $Tj,p=k1(\text{problem size})+k2(\text{problem size})+\ldots$ where ki are the algorithmic steps performed in data parallel fashion by the $p^{th}$ process in superstep j.

2. Hybrid supersteps $$Tj=\max(Tj,1,Tj,2,\ldots,Tj,p)$$

where $Tj,p=\max(k1(\text{problem size, resources})+k2(\text{problem size, resources}))+\ldots$ where ki are the algorithmic steps performed in task parallel fashion by the $p^{th}$ process using some resources in superstep j.

The runtime costs for each superstep along with possible overhead costs in each superstep may be added and categorized into three categories: Serial Time (Ts), Parallel Time (Tp) and Overhead Time (To).

The parallel and overhead times (Tp+To) may be further analyzed to look for optimizable algorithmic tasks and the root causes of the overhead costs to design and implement several optimization techniques that minimize the overhead costs and boost the parallel terms for improved performance. The serial time (Ts) may be pruned out of the optimization in cases where serial optimization potential is low. The optimization techniques implemented may include Data Buffering, Task Scheduling, Sampling, and Load Balancing.

Data Buffering optimization may account for minor speed mismatch between parallel subtasks in hybrid task and data parallel supersteps (e.g., supersteps 3 and 4). Data flow between parallel sub-tasks is implemented via buffers to allow for producer tasks and consumer tasks to keep working without waiting. The data buffers may be recycled to avoid memory fragmentation.

Task Scheduling optimization may improve dynamic control of resources allocated to parallel sub-tasks in hybrid task and data parallel supersteps (e.g., superstep 3). A double exponential smoothing based forecast-based task scheduling algorithm may forecast speed mismatches between producer sub-tasks and consumer sub-tasks and then re-allocate available CPU resources among them to improve performance.

Sampling optimization may minimize the data I/O and communication between parallel processes of HiCOPS. A sampling technique may reduce the footprint of the partial result data computed at each parallel process, before being accumulated (e.g., in superstep 4.)

Load Balancing optimization may improve on an already existing load balancing algorithm for database partitioning, (e.g., as described in Haseeb et al., LBE: A computational load balancing algorithm for speeding up parallel peptide search in mass-spectrometry based proteomics, In 2019 IEEE International Parallel and Distributed Processing Symposium Workshops (IPDPSW), pages 191-198, IEEE, 2019, which is hereby incorporated by reference herein in its entirety) and use the improved algorithm to implement load balancing between the parallel HiCOPS tasks in a static manner.

An embodiment of HiCOPS has been implemented using C++ 14, Python, and Bash. Instrumentation is in-built using Timemory framework for performance analysis and optimizations.

Several other optimization techniques and the algorithms pertinent to each superstep are described below. Additional optimization techniques and the algorithms pertinent to various aspects of HiCOPS may be employed by one of ordinary skill in the art. A task-mapping algorithm that may construct and map the parallel HiCOPS Message Passing Interface (MPI) processes on to the distributed memory cluster is also discussed below.

For comparison, related art Naive Approaches to HPC database peptide search methods follow an inherently serial design where they may replicate the shared memory workflow on a distributed memory system. This may entail replication of the entire database (which may be between hundreds of GB to a few TBs in size) on each parallel node in the system. The experimental data may then also be split between the parallel instances (replicating the entire serial workflow). This deign can be simply viewed as running the original software on a set of computers, with a sub-set of the experimental data—without taking any advantage of the underlying distributed memory system itself.

Embodiments of the subject invention completely overhaul the design and beneficially make use of the distributed memory and a higher memory bandwidth available on these architectures by splitting the workload between parallel nodes (split the massive database and relevant data structures), performing partial computations much faster and merging in an advantageous way that minimizes impact to the overall system performance.

Embodiments have been measured to provide more than 100× improvement compared to many existing shared and distributed memory tools, especially when the dataset and database are big (e.g., database is larger than 50 million peptides and/or dataset is larger than 1 million spectra).

Performing extreme scale peptide identification experiments at ultra-fast speeds, it has been demonstrated that embodiments are capable of searching gigabytes of experimental data against hundreds of gigabytes to terabytes of database content in a few minutes, whereas existing tools may require days or weeks to complete the same search. Embodiments are generic and may be adapted to additional existing tools and workflows through a re-design to achieve ultra-fast speeds similar to results presented herein.

The software framework of the subject invention may implement parallel versions of many algorithms and data structures that can serve as building blocks for implementation of novel algorithms on top of the parallel core design.

Proteomics and systems biology experiments and discoveries may use the subject invention to speed up their analyses and research. Data used in the experiments presented herein was obtained from: UniProt (uniprot.org) and Pride Archive (www.ebi.ac.uk/pride/archive/), both of which are public data repositories where the data are available under no agreements, and both of which are hereby incorporated by reference herein in their respective entireties.

In one embodiment, less than 0.5% of required source code was modified and used from public GitHub repositories under open source licenses (e.g., MIT or GPL). The original license and author information was maintained intact in the relevant source code files.

Also utilized were freely available open source resources including the C++ standard library, OpenMP, MPI, CMake and Timemory libraries and Python packages (e.g., numpy, matplotlib etc.). It is contemplated within the scope of the invention to incorporate additional C++ and Python libraries (e.g., Boost, LAPACK, Kokkos, UPC++, Pybind11, MPI4Py, etc.) in future development.

Also used was the MSconvert tool (hub.docker.com/r/chambm/pwiz-skyline-i-agree-to-the-vendor-licenses) wrapped in a custom Bash based tool to convert experimental data into specific formats. Users may use the MSconvert tool directly to do so. The custom Bash based tool of the subject invention beneficially automates the process to enhance usability and efficiency. All tools, packages, libraries, data sources, databases, data structures, or other utilities or accessories used with or incorporated into HiCOPS or any embodiment (e.g., opensource, free, or unlicensed) throughout this disclosure are hereby incorporated by reference herein in their respective entireties.

Embodiments provide novel efficient parallel computational methods, and their implementation on memory-distributed architectures for peptide identification tool called HiCOPS, that enable more than 100-fold improvement in speed over most existing HPC proteome database search tools. HiCOPS empowers the supercomputing database search concept for comprehensive identification of peptides, and all their modified forms within a reasonable time frame. Searching Gigabytes of experimental MS data against Terabytes of databases, HiCOPS completes peptide identification in few minutes using 72 parallel nodes (1728 cores) compared to several weeks required by existing state-of-the-art tools using 1 node (24 cores); 100 minutes vs 5 weeks=500× improvement in speed. Also provided is a theoretical framework for an overhead-avoiding strategy, and superior performance evaluation results for key metrics including execution time, CPU utilization, improvement in speed, and I/O efficiency. Embodiments demonstrate superior performance as compared to all existing HPC strategies.

Faster and more efficient peptide identification algorithms have been the cornerstone of computational research in shotgun MS based proteomics for more than 30 years. Millions of raw, noisy spectra can be produced in a span of few hours, using modern mass spectrometry technologies producing several gigabytes of data (e.g., FIG. 6). Database peptide search is the most commonly employed computational approach to identify the peptides from the experimental spectra. In this approach, the experimental spectra are searched against a database of model-spectra (or theoretical-spectra) with the goal to find the best possible matches. The model-spectra database is simulated through in-silico techniques using a proteome sequence database (FIG. 7). The model-spectra database can grow exponentially in space (e.g., several gigabytes to terabytes) as the post-translational modifications (PTMs) are incorporated in simulation. Therefore, the cost of moving and managing this data to match with the spectra now exceeds the costs of doing the arithmetic operations in these search engines leading to non-scalable workflows with increasingly larger and complex data sets.

As demonstrated by other big data fields, such limitations can be reduced by developing parallel algorithms that combine the computational power of thousands of processing elements across distributed-memory clusters, and supercomputers. HPC techniques for processing of MS data can be used for multicore and distributed-memory architectures. Similar to serial algorithms, the objective of these HPC methods has been to speed up the arithmetic scoring part of the search engines, by spawning multiple (managed) instances of the original code, replicating the theoretical database, and splitting the experimental data. However, computationally optimal HPC algorithms that minimize both the computational and communications costs for these tasks are still needed. Urgent need for developing methods that exhibit optimal performance has been illustrated in theoretical frameworks (e.g., Saeed, Communication lower-bounds for distributed-memory computations for mass spectrometry based omics data, arXiv preprint arXiv:2009, 14123, 2020, which is hereby incorporated by reference herein in its entirety), and can potentially lead to large-scale systems biology studies especially for meta-proteomics, proteogenomic, and MS based microbiome or non-model organisms' studies having direct impact on personalized nutrition, microbiome research, and cancer therapeutics.

In order to develop faster strategies applicable to MS based omics data analysis, embodiments provide novel HPC frameworks that provide orders-of-magnitude faster processing over both serial and parallel tools. Also provided is a new HPC tool, capable of scaling on large (distributed) symmetric multiprocessor (SMP) supercomputers. HiCOPS makes searches possible (e.g., completing in a few minutes) even for terabyte level theoretical database(s); something not feasible (e.g., requiring several weeks of computations) with existing state-of-the-art methods. HiCOPS's utility has been demonstrated in both closed- and open-searches across different search-parameters, and experimental conditions. Further, experimental results depict more than 100× improvement in speed for HiCOPS compared to several existing shared and distributed memory database peptide search tools. Embodiments may utilize an overhead-avoiding strategy that splits the database (algorithmic workload) among the parallel processes in a load balanced fashion, executes the partial database peptide search, and merges the results in communication optimal way, alleviating the resource upper bounds that exist in existing database peptide search tools.

Results have been demonstrated on several data- and compute-intensive experimental conditions including using 4 TB of theoretical database against which millions of spectra were matched. HiCOPS, even when using similar scoring functions, outperforms both parallel and serial methods. In one example an embodiment searching 41 GB of experimental spectra against a database size of 1.8 TB ran in only 103.5 minutes using 72 parallel nodes compared to MSFragger which took about 35.5 days to complete the same experiment on 1 node (494× slower). HiCOPS completed an open-search (dataset size: 8K spectra, database size: 93.5M spectra) in 144 seconds as compared to the X!! Tandem (33 minutes) and SW-Tandem (4.2 hours), all using 64 parallel nodes; demonstrating that HiCOPS may outperform existing parallel tools. In another example 12 different experiment sets were used to demonstrate the performance of an embodiment of a parallel computing framework of the subject invention using metrics such as parallel efficiency: 70-80%, load imbalance cost: ≤10%, CPU utilization: improved with parallel nodes, communication costs: ≤10%, I/O costs: ≤5% and task scheduling related costs: ≤5%; to demonstrate superior performance as compared to existing serial or parallel solutions. Embodiments are not limited to data from a particular MS instrument. Embodiments allow searches on multiple model species databases and can be incorporated into existing data analysis pipelines. Embodiments provide the first software pipeline capable of efficiently scaling to the terabyte-scale workflows using large number of parallel nodes (e.g., in a database peptide search domain.)

Results

HiCOPS constructs the parallel database peptide search algorithmic workflow (task-graph) using four Single Program Multiple Data (SPMD) Bulk Synchronous Parallel (BSP) supersteps (e.g., as disclosed in Valiant, A bridging model for parallel computation, Communications of the ACM, 33(8):103-111, 1990, which is hereby incorporated by reference herein in its entirety); where a set of processes (pi E P) execute ($\varphi$) supersteps in asynchronous parallel fashion and synchronize between them. As shown in FIG. 1, an embodiment may allow searching of a partial theoretical database in parallel; something that has not been accomplished in the context of existing peptide database-search tools. These partial search-results are then merged using a communication-optimal technique.

Figure 2:
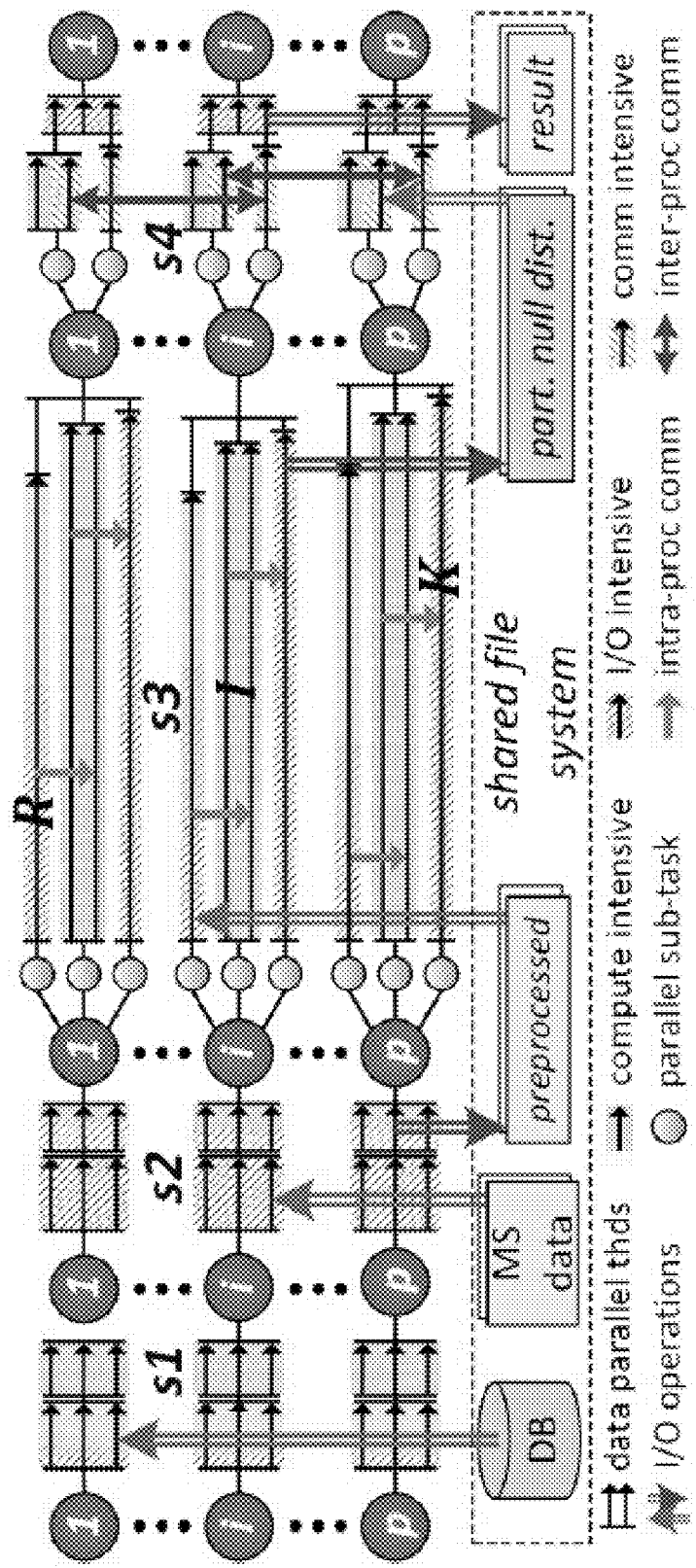
FIG. 2 is a schematic diagram representing a Workload Profile, according to an embodiment of the subject invention.

In the first superstep, the massive model-spectra database is partitioned across parallel processes in a load balanced fashion. In the second superstep, the experimental data are divided into batches and pre-processed if required. In the third superstep, the parallel processes execute a partial database peptide search on the pre-processed experimental data batches, producing intermediate results. In the final superstep, these intermediate results are de-serialized and assembled into complete (e.g., global) results. The statistical significance scores are computed (Online Methods, FIG. 1) using global results. FIG. 2 gives an overview of the parallelization scheme, task-graph, and workload profile for each of the supersteps (Online Methods).

The total wall time ($T_H$) for executing the four supersteps is the sum of superstep execution times, given as:

$$T_H = T_1 + T_2 + T_3 + T_4$$

Where the execution time for a superstep (j) is the maximum time required by any parallel task ($p_i \in P$) to complete that superstep, given as:

$$T_j = \max(T_{j,p_1}, T_{j,p_2}, \ldots, T_{j,p_p})$$

Or simply:

$$T_j = \max_{p_i}(T_{j,p_i})$$

Combining the above three equations, the total HiCOPS runtime is given as:

$$T_H = \sum_{j=1}^{4} \max_{p_i}(T_j, p_i) \quad (1)$$

Experimental Setup

The following datasets from Pride Archive were used for experimentation and evaluation purposes.
- $E_1$: PXD009072 (0.305 million spectra)
- $E_2$: PXD020590 (1.6 million spectra)
- $E_3$: PXD015890 (3.8 million spectra)
- $E_4$: PXD007871, 009072, 010023, 012463, 013074, 013332, 014802, and 015391 combined (1.515 million spectra)
- $E_5$: All above datasets combined (6.92 million spectra)

The search experiments were conducted against the following protein sequence databases. The databases were digested in-silico using Trypsin as enzyme with 2 allowed missed cleavages, peptide lengths between 6 and 46 and peptide masses between 500 and 5000 Da. The number and type of PTMs added to the database, and the peptide precursor mass tolerance ($\delta M$) were varied across experiments however, the fragment mass tolerance (dF) was set to ±0.005 Da in all experiments.
- $D_1$: UniProt *Homo sapiens* (UP005640)
- $D_2$: UniProt SwissProt (reviewed, multi-species)

Twelve different experiments were designed using combinations of the above-mentioned databases, datasets and experimental parameters for an extensive performance evaluation. These experiments exhibit varying experimental workloads to cover a wide range of real-world scenarios. Each of these experiment sets is represented using a tuple: en=(q, D, $\delta M$) where q is dataset size in 1 million spectra, D is model-spectra database size in 100 million spectra and $\delta M$ peptide precursor mass setting in ±100 Da to represent the problem size. The designed experiment sets (of varying workloads) are listed as: e1=(0.3, 0.84, 0.1), e2=(0.3, 0.84, 2), e3=(3.89, 0.07, 5), e4=(1.51, 2.13, 5), e5=(6.1, 0.93, 5), e6=(3.89, 7.66, 5), e7=(1.51, 19.54, 5), e8=(1.6, 38.89, 5), e9=(3.89, 15.85, 5), e10=(3.89, 1.08, 5), e11=(1.58, 2.13, 1), and e12=(0.305, 0.847, 5).

Runtime Environment: All distributed memory tools were run on the Extreme Science and Engineering Discovery Environment (XSEDE) (Towns et al., Xsede: accelerating scientific discovery, Computing in Science & Engineering, 16(5):62-74, 2014, which is hereby incorporated by reference herein in its entirety), Comet cluster at the San Diego Supercomputer Center (SDSC). All Comet compute nodes are equipped with 2 sockets×12 cores of Intel Xeon E5-2680v3 processor, 2 NUMA nodes×64 GB DRAM, 56 Gbps FDR InfiniBand interconnect and Lustre shared file system. The maximum number of nodes allowed per job is 72 and maximum allowed job time is 48 hours. The shared memory tools, on the other hand, were run on a local server system equipped with an Intel Xeon Gold 6152 processor (22 physical cores, 44 hardware threads), 128 GB DRAM and a local 6 TB SSD storage as most experiments using the shared memory tools required >48 hours (job time limit on XSEDE Comet).

Correctness of the parallel design was evaluated by searching all five datasets $E_i$ against both protein sequence databases Di under various settings, and combinations of PTMs. The correctness was evaluated in terms of consistency in the number of database hits, the identified peptide to spectrum matches (PSM), and the hyper-scores and e-values assigned to those sequences (within 3 decimal points) for each experimental spectrum searched. The experiments were performed using combinations of experimental settings wherein were observed more than 99.5% consistent results regard-less of the number of parallel nodes. The negative error in expected values results observed in erroneous identifications was caused by the sampling, and floating-point precision losses (Online Methods, FIGS. 5 and 1D). A snippet of the 251,501 peptide to spectrum match (PSM) results obtained by searching the dataset: $E_1$ against the database: $D_1$ with no post-translational modifications added at precursor mass tolerance: $\delta M = \pm 500$ Da is shown in Table 1.

TABLE 1

A snippet of the peptide-to-speactrum matches (PSMs) and e-values obtained by searching the dataset: $E_1$ against database: $D_1$ (no mods, $\delta M$ = 500 Da). Full table can be requested from the corresponding author.

| Matched Peptide | e-Values for Parallel nodes | | | | |
|---|---|---|---|---|---|
| | 1 | 2 | 4, 8 | 16, 32 | 64 |
| HLTYENVER | 6.6e−5 | 6.5e−5 | 6.5e−5 | 6.5e−5 | 6.5.e−5 |
| SEGESSRSVR | 3.175e−3 | 3.174e−3 | 3.174e−3 | 3.175e−3 | 3.174e−3 |
| IFQCNKHMK | 0.037038 | 0.037037 | 0.037037 | 0.037036 | 0.037037 |
| FIVSKNK | 0.113302 | 0.113301 | 0.113298 | 0.113297 | 0.113297 |
| QQIVSGR | 1.294027 | 1.293975 | 1.293975 | 1.293975 | 1.293975 |
| STVASMMHR | 2.641636 | 2.64151 | 2.64151 | 2.64151 | 2.64151 |
| TLFKSSLK | 7.000016 | 7.0 | 7.0 | 7.0 | 7.0 |
| QKQLLKEQK | 16.856401 | invalid | | 16.855967 | invalid |

Comparative analysis reveals orders of magnitude improvement in speed, comparing the HiCOPS speed against many existing shared and distributed memory parallel database peptide search algorithms including: MSFragger v3.0 (Kong et al., Msfragger: ultrafast and comprehensive peptide identification in mass spectrometry-based proteomics, Nature Methods, 14(5):513, 2017; which is hereby incorporated by reference herein in its entirety);

X! Tandem v17.2.1 (Craig et al., Tandem: matching proteins with tandem mass spectra, Bioinformatics, 20(9): 1466-1467, 2004), which is hereby incorporated by reference herein in its entirety;

Tide/Crux v3.2 (McIlwain et al., Crux: rapid open source protein tandem mass spectrometry analysis, Journal of proteome research, 13(10):4488-4491, 2014; which is hereby incorporated by reference herein in its entirety);

X!! Tandem v10.12.1 (Bjornson et al., X!! tandem, an improved method for running x! tandem in parallel on collections of commodity computers, The Journal of Proteome Research, 7(1):293-299, 2007; which is hereby incorporated by reference herein in its entirety); and SW-Tandem (Li et al., Mctandem: an efficient tool for large-scale peptide identification on many integrated core (mic) architecture, BMC bioinformatics (Oxford, England) 2019; which is hereby incorporated by reference herein in its entirety).

In the first experiment set, a subset of 8,000 spectra (file: 7 Sep. 2018 Olson WT24) from dataset: $E_3$ was searched against the database: $D_2$. Fixed Cysteine Carbamidomethylation, and variable Methionine oxidation, and Tyrosine Biotin-tyramide were added yielding model-spectra database of 93.5 million (~90 GB). In the second experiment set, the entire dataset: $E_3$ was searched against the same database $D_2$. The peptide precursor mass tolerance was in both sets was first set to: $\delta M = \pm 10$ Da and then $\pm 500$ Da ($\pm 100$ Da for Tide/Crux). The obtained wall time results (e.g., Tables 2, 3, 4, 5) show that HiCOPS outperforms both the shared and distributed memory tools (in speed) by >100× when the experiment size is large.

For instance, as seen in the tables above for the second experiment, HiCOPS outperforms both the X!!Tandem and SW-Tandem by >800× (230 seconds v >2 days) using 64 nodes. HiCOPS also depicts improvements in speed of 67.3× and 350× versus MSFragger (1 node) for the same experiment set. Furthermore, no improvements in speed were observed for SW-Tandem with increasing number of parallel nodes (no parallel efficiency). Repeated efforts were made to contact the corresponding authors about the parallel efficiency issue but no response was received prior to drafting of this specification (See, e.g., Example 6).

TABLE 2

Speed comparison between existing tools and HiCOPS for the experiment 1a, dataset size: 8 K, database size: 93.5 M, precursor mass tolerance: $\delta M = 10.0$ DA.

| Search Tool | Execution Time (s) for parallel nodes | | | | |
|---|---|---|---|---|---|
| | 1 | 2 | 4 | 8 | 16 |
| HiCOPS | — | 166.32 | 126.35 | 113.53 | 134.86 |
| X!!Tandem | 4980 | 2445 | 1279.8 | 690 | 360 |
| SW-Tandem | 1015 | 992 | 1002 | 999 | 1019 |
| MSFragger | 299.4 | — | — | — | — |
| X!Tandem | 957 | — | — | — | — |
| Crux/Tide | 2470 | — | — | — | — |

TABLE 3

Speed comparison between existing tools and HiCOPS for the experiment 1b, dataset size: 8K, database size: 93.5M, precursor mass tolerance: $\delta M = 500.0$ Da.

| Search Tool | Execution Time (s) for parallel nodes | | | | | | |
|---|---|---|---|---|---|---|---|
| | 1 | 2 | 4 | 8 | 16 | 32 | 64 |
| HiCOPS | — | 188 | 135 | 115 | 101 | 101 | 144 |
| X!!Tandem | 115K | 57.7K | 29.05K | 14.6K | 7.4K | 3.72K | 1.98K |
| SW-Tandem | 19.99K | 17.1K | 15.4K | 14.3K | 15.1K | 15K | 15K |
| MSFragger | 521 | — | — | — | — | — | — |
| X!Tandem | 18.65K | — | — | — | — | — | — |
| Crux/Tide | segmentation fault | | | | | | |

The application of HiCOPS in extremely resource intensive experimental settings (e.g., large-scale peptide identification) was demonstrated using additional experiments where the datasets: $E_3$, $E_4$ and $E_2$ were searched against model-spectra databases of sizes: 766M (780 GB), 1.59B (1.7 TB) and 3.88B (4 TB) respectively ($\delta M = \pm 500$ Da). HiCOPS completed the execution of these experiments using 64 parallel nodes (1538 cores) in 14.55 minutes, 103.5 minutes, and 27.3 minutes, respectively. To compare, the second experiment (dataset: $E_4$ and database size: 1.59B (1.7 TB)) was searched on MSFragger which completed after 35.5 days making HiCOPS 494× faster. The rest of the experiments were intentionally not run using any other tools but HiCOPS to avoid feasibility issues as each tool would require several months of processing to complete each experiment, as evident from Tables 3, 4, 5. The wall clock execution time results for this set of experiments are summarized in the Table 6.

TABLE 4

Speed comparison between HiCOPS and existing tools for the experiment 2a, dataset size: 3.8M, database size: 93.5M, precursor mass tolerance: $\delta M = 10.0$ Da. X!!Tandem and SW-Tandem ran for 2 days in all parallel configurations but failed to complete and were terminated by SLURM due to max job time limit on XSEDE Comet system.

| Search Tool | Execution Time (s) for parallel nodes | | | | |
|---|---|---|---|---|---|
| | 1 | 2 | 4 | 8 | 18 |
| HiCOPS | — | 557.549 | 371.585 | 262.16 | 213.622 |
| X!!Tandem | terminated after 2 days | | | | |
| SW-Tandem | terminated after 2 days | | | | |
| MSFragger | 13402.66 | — | — | — | — |
| X!Tandem | 1.71M | — | — | — | — |
| Crux/Tide | 875.5K | — | — | — | — |

TABLE 5

Speed comparison between HiCOPS and existing tools for the experiment 2b, dataset size: 3,8M, database size: 93.5M, precursor mass tolerance: $\delta M = 500.0$ Da. X!!Tandem and SW-Tandem ran for 2 days in all parallel configurations but failed to complete and were terminated by SLURM due to max job time limit on XSEDE Comet system. X!Tandem has been running for 75 days at the time of submission of this manuscript and is expected to run over 8 months to complete its execution.

| Search Tool | Execution Time (s) for parallel nodes | | | | | | |
|---|---|---|---|---|---|---|---|
| | 1 | 2 | 4 | 8 | 16 | 32 | 64 |
| HiCOPS | — | 23.5K | 66K | 2.8K | 1.4K | 807 | 485 |
| X!!Tandem | terminated after 2 days | | | | | | |
| SW-Tandem | terminated after 2 days | | | | | | |
| MSFragger | 170.1K | — | — | — | — | — | — |
| X!Tandem | 75 days* | — | — | — | — | — | — |
| Crux/Tide | segmentation fault | | | | | | |

HiCOPS exhibits efficient strong-scale improvements in speed. The improvement in speed and strong scale efficiency for the overall and superstep-by-superstep runtime was measured for all 12 experiment sets. The results (FIGS. 9, 3A, and 3B) depict that the overall strong scale efficiency closely follows the superstep 3 (evident in FIG. 9) and ranges between 70-80% for sufficiently large experimental workload. Super-linear improvements in speed were also observed in many experiments with higher workloads. The following hardware counters-based metrics were also recorded for all experiment sets: instructions per cycle (ipc), last level cache misses per all cache level misses (lpc), and the cycles stalled due to writes per total stalled cycles (wps). The results (FIG. 3C) show that the CPU, cache, and memory bandwidth utilization improves as the workload per node (wf/P) increases reaching to an optimum point after which it saturates due to memory bandwidth contention since the database search algorithms employed (and also in general) are highly memory intensive. Beyond this saturation point, increasing the number of parallel nodes for the same experimental workload resulted in a substantial improvement (super-linear) in performance as the workload per node (wf/P) reduced to the normal (optimal) range. For instance, the experiment set e5 depicts super-linear improvements in speed (FIG. 3A) which can be correlated to the hardware performance surge in FIG. 3C. Performance evaluation reveals minimal overhead costs where HiCOPS searches a variety of high intensity workload test data sets. The load imbalance, communication, I/O, and task scheduling costs were measured for all experiments (12 designed experiment sets.) The obtained results (FIGS. 4A-4C) depict that the load imbalance costs remain ≤10%, communication costs remain ≤5%, I/O costs remain ≤10% in most experiments. Load imbalance may be interpreted as a direct measure of synchronization cost. The task-scheduling cost was measured through a time series (twait) (FIG. 4E) which monitors the time that the parallel cores had to wait for the data I/O to complete. The results (FIG. 4E) depict that the task-scheduling algorithm actively performs counter measures (reallocates threads) as soon as a surge in wait-time is detected keeping the cost to ≤5% in most experiments (FIG. 4D). It was also observed that the I/O cost is affected by a number of factors including average dataset file size, number of files in the dataset and the available file system bandwidth. The communication cost is affected by the available network bandwidth.

Enormous possibilities of chemical and biological modifications add knowledge discovery dimensions to mass spectrometry-based omics but are not explored in most studies, in part, due to the scalability challenges associated with comprehensive PTM searches. Related art MS based computational proteomics algorithms, both serial and parallel, have focused on improving arithmetic computations by introducing indexing and approximation methods to speed up their workflows. However recent trends in the workloads stemming from systems biology (e.g. meta-proteomics, proteogenomics) experiments point towards urgent need for computational tools capable of efficiently harnessing the compute and memory resources from supercomputers. The highly scalable and low-overhead strategy, HiCOPS, meets this urgent need for next generation of computational solutions leading to more comprehensive peptide identification application. Further, this HPC framework can be adapted for accelerating most existing modern database peptide search algorithms.

TABLE 6

Experimental wall times for large-scale peptide identification experiments using HiCOPS and MSFragger.
Exp. 1: (DB: 766M, DS:3.8 M, δM = 500Da),
Exp. 2: (DB: 1.6B, DS: 1.5M, δM = 500Da),
Exp. 3: (DB: 3.88B, DS: 1.6M, δM = 500Da).
The experiments were not performed using other tools due to their relatively slower speeds requiring several months of processing per tool per experiment.

| Exp. Num | Tool | Nodes | Dataset (GB) | Database (GB) | Time (min) |
|---|---|---|---|---|---|
| 1 | HiCOPS | 64 | 20 | 780 | 14.55 |
| 2 | HiCOPS | 64 | 15 | 1692 | 103.5 |
| 3 | MSFragger | 1 | 15 | 1692 | 51130 |
| 3 | HiCOPS | 64 | 41 | 4000 | 27.3 |

Embodiments are demonstrated using novel experiments, peptide deduction through searching gigabytes of experimental tandem MS (MS/MS) data against terabytes of model-spectra databases in only a few minutes compared to several days required by modern tools (100 minutes vs 5 weeks; 500× improvement in speed using 72 parallel nodes). The overhead-avoiding BSP-model based parallel algorithmic design allows efficient exploitation of extreme-scale resources available in modern high-performance computing architectures, and supercomputers. Extensive performance evaluation using over two dozen experiment sets with variable problem size (database and dataset sizes) and experimental settings revealed superior strong scale parallel efficiency, and minimal overhead costs for HiCOPS. The provided novel HPC framework gives systems biologist a tool to perform comprehensive modification searches for meta-proteomics, proteogenomic, and proteomics studies for non-model organisms at scale. HiCOPS is under direct development and contemplates improved I/O efficiency, load balancing, reduced overhead costs, and the parallel design for heterogeneous and CPU-GPU architectures in future versions. The peptide search strategy (both open- and closed) for comprehensive PTM's, made practical by HiCOPS, has the potential to become a valuable option for scalable analysis of shotgun Mass Spectrometry based omics.

Turning now to the figures, FIG. 1 is a schematic diagram representing a high-performance computing database peptide search process in accordance with an embodiment of the subject invention. The process may be represented as four Supersteps shown in panels a, b, c, and d of FIG. 1 with arrows representing data flow between the Supersteps. In panel (a) Superstep 1: The massive model-spectra database (shown as shapes) is partitioned among parallel MPI processes in load balanced manner and then locally indexed. In panel (b) Superstep 2: The experimental MS/MS spectra data are split, indexed, tagged, pre-processed and written back to the file system in parallel. In panel (c) Superstep 3: The partial database peptide search pipeline executed by all parallel processes is shown. On each process, three parallel sub-tasks R, I and K work in producer-consumer pipeline to load the pre-processed data, execute the partial database search producing partial results, and write the (sampled) results to the shared memory respectively. The available threads are managed between parallel sub-tasks through a task scheduling algorithm. The sub-tasks communicate via buffer queues to avoid fragmentation. (d) Superstep 4: The partial results are assembled into complete results to compute statistical scores which are communicated to their origin processes. A Legend panel defines markers for parallel process, parallel sub-task, thread, compute, I/O, communications, parallel processing, and control elements throughout FIG. 1.

Embodiments partition large databases into small but identical partitions that are processed on parallel nodes (e.g., the data in each partition, while not identical or directly replicated, would roughly look similar). By way of analogy, assume a set of 10 pizzas all with different toppings and sauces. In order to partition the database of pizzas among 5 people, each partition can have a ⅕th sized pizza slice from each of the 10 pizzas; this way all partitions will have more or less a similar amount and kind of toppings.

FIG. 2 is a schematic diagram representing a Workload Profile in accordance with an embodiment of the subject invention. Each row (e.g., as indicated by the riw index/counters 1, . . . i, . . . p within the filled-circles) processes independently through all Supersteps (s1, s2, s3, s4) in a horizontal fashion except where communication between rows is indicated by vertical arrows. Embodiments may provide any number up to p rows (e.g., i=1, 2, 3, . . . , p; where p is a positive integer) depending on the size of the data and available resources. Supersteps s1 and s2 are designed as data parallel. Supersteps s3 and s4 are designed as hybrid task and data parallel. The workload executed by the four respective supersteps are (s1) compute intensive, (s2) I/O intensive, (s3) mixed (compute and I/O), and (s4) mixed (compute and comm.), respectively. In the last two supersteps, the compute workload may supersede the communication and/or I/O, given that the associated overhead costs are overlapped or minimized. A Legend below the schematic defines markers for data parallel threads, compute intensive, I/O intensive, communication intensive, I/O operations, parallel sub-task, intra-process communication, and inter-process communications elements throughout FIG. 2.

Figure 3A:
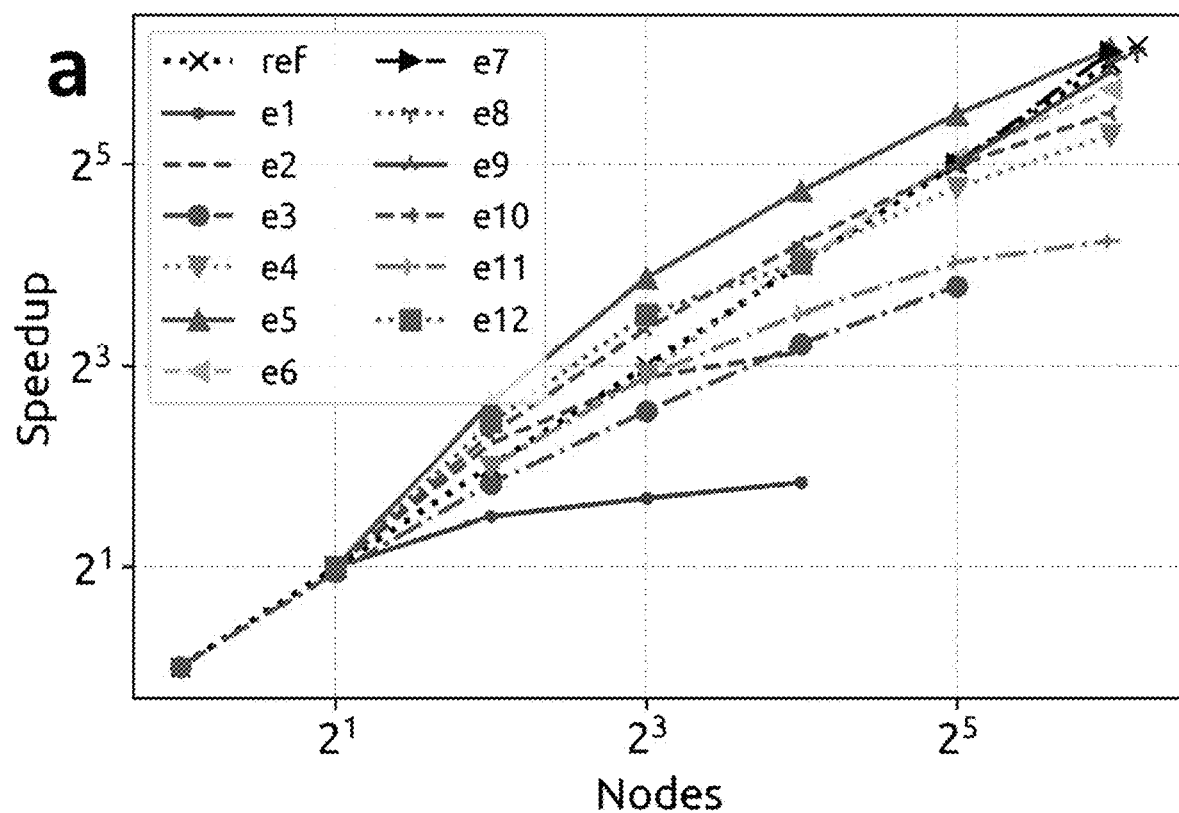
FIGS. 3A-3C are a series of performance metric charts for 12 designed experiment sets labelled e1 through e12.
Figure 3B:
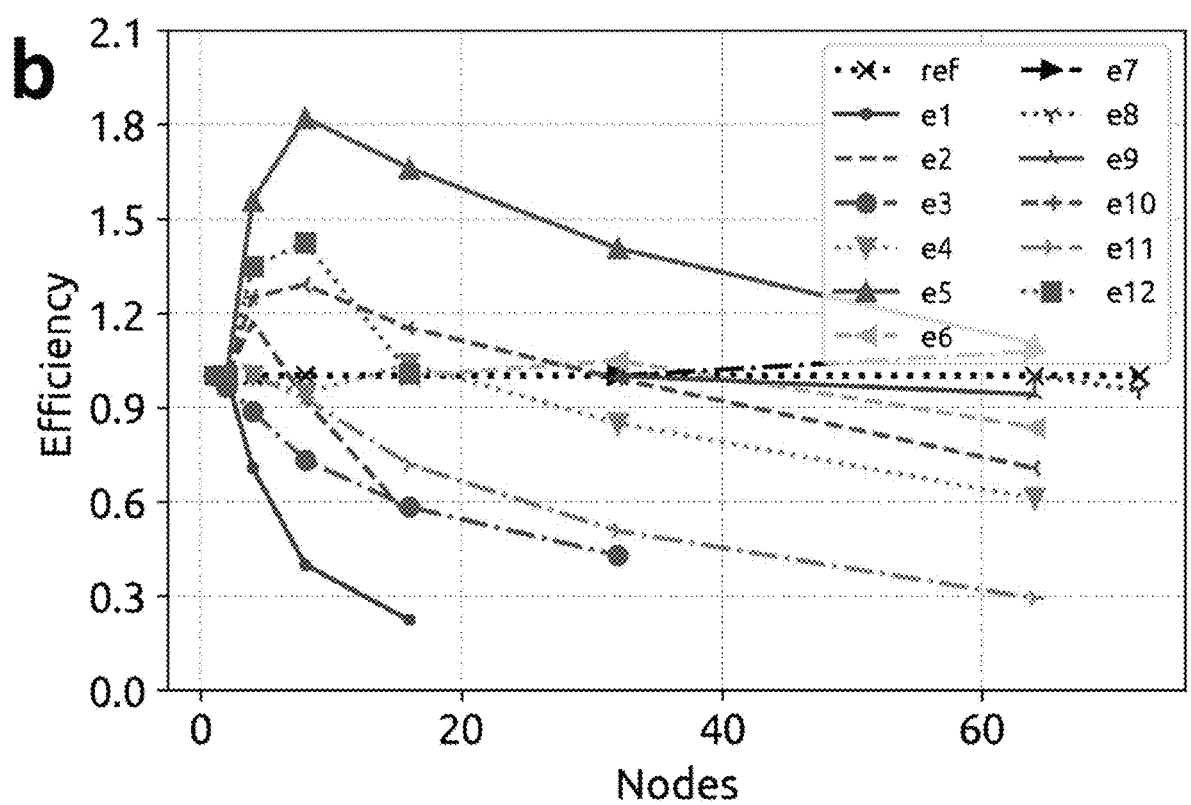
Figure 3C:
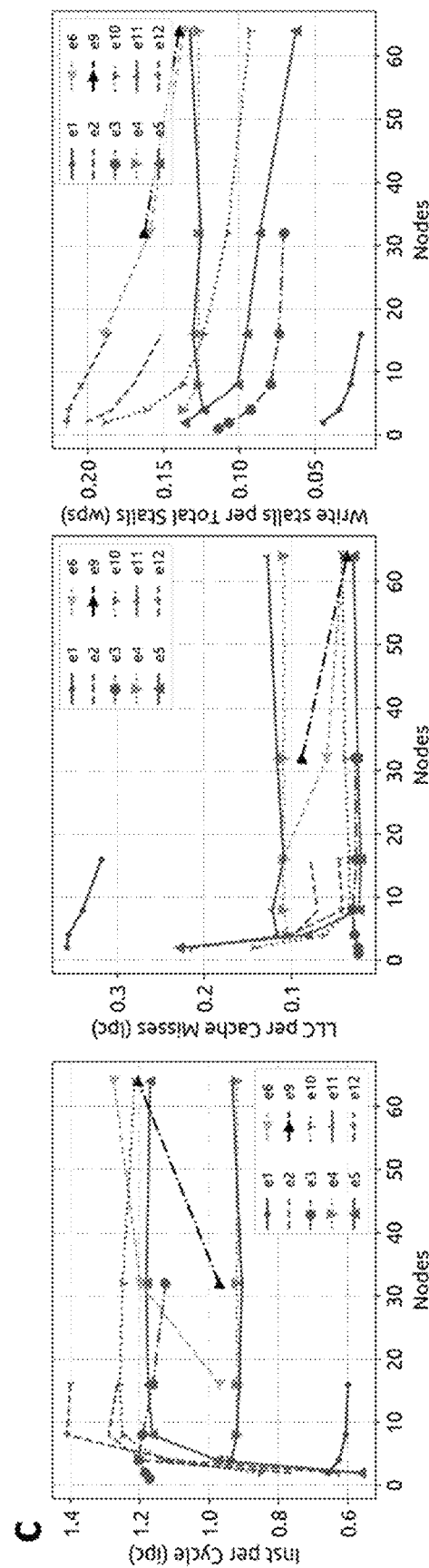

FIGS. 3A-3C are a series of performance metric charts for 12 designed experiment sets labeled e1 through e12. In FIGS. 3A and 3B a reference experiment set is also shown. In FIG. 3A the reference experiment set shows a 1-to-1 speed improvement per additional Node. In FIG. 3B the reference experiment set shows an efficiency of 1.0 across all Nodes. In FIG. 3A the speed improves (improvement in speed may be denoted as "speedup" on the y-axis legend in this figure and throughout the specification) as the experimental workload increases ranging between 70-80% for most experiment sets. In FIG. 3B the parallel efficiency improves as the experimental workload increases ranging between 70-80% for most experiment sets. In FIG. 3C the hardware utilization metrics show an improved performance per node trend for large workloads as the number of parallel nodes increase resulting in super-linear improvements in speed (e.g., e5).

Figure 4A:
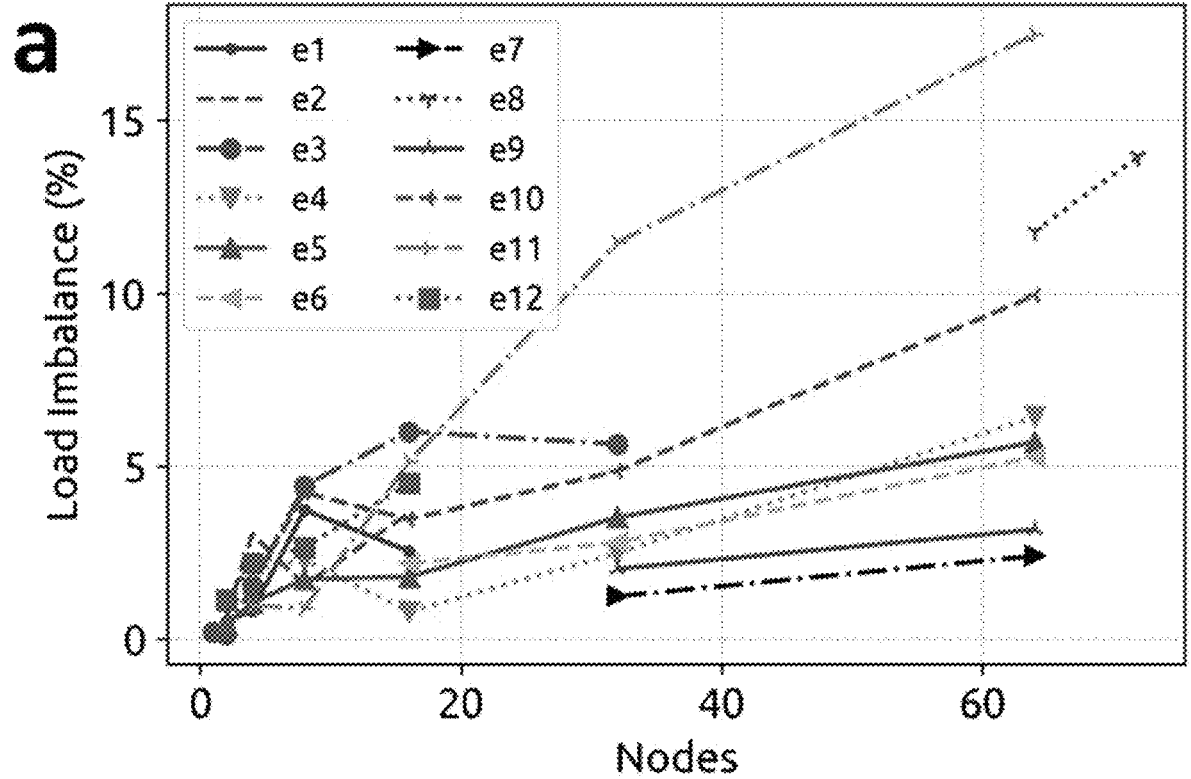
FIGS. 4A-4E are a series of performance metric charts for 12 designed experiment sets labelled e1 through e12.
Figure 4B:
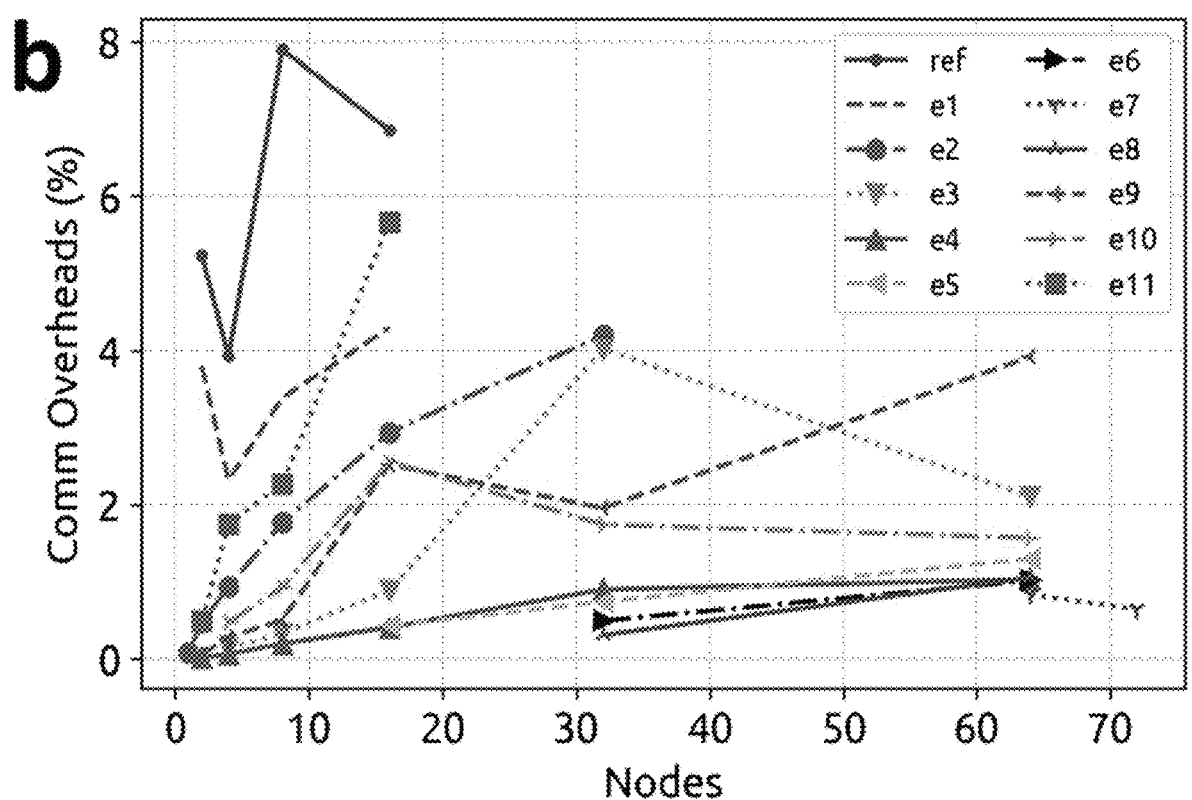
Figure 4C:
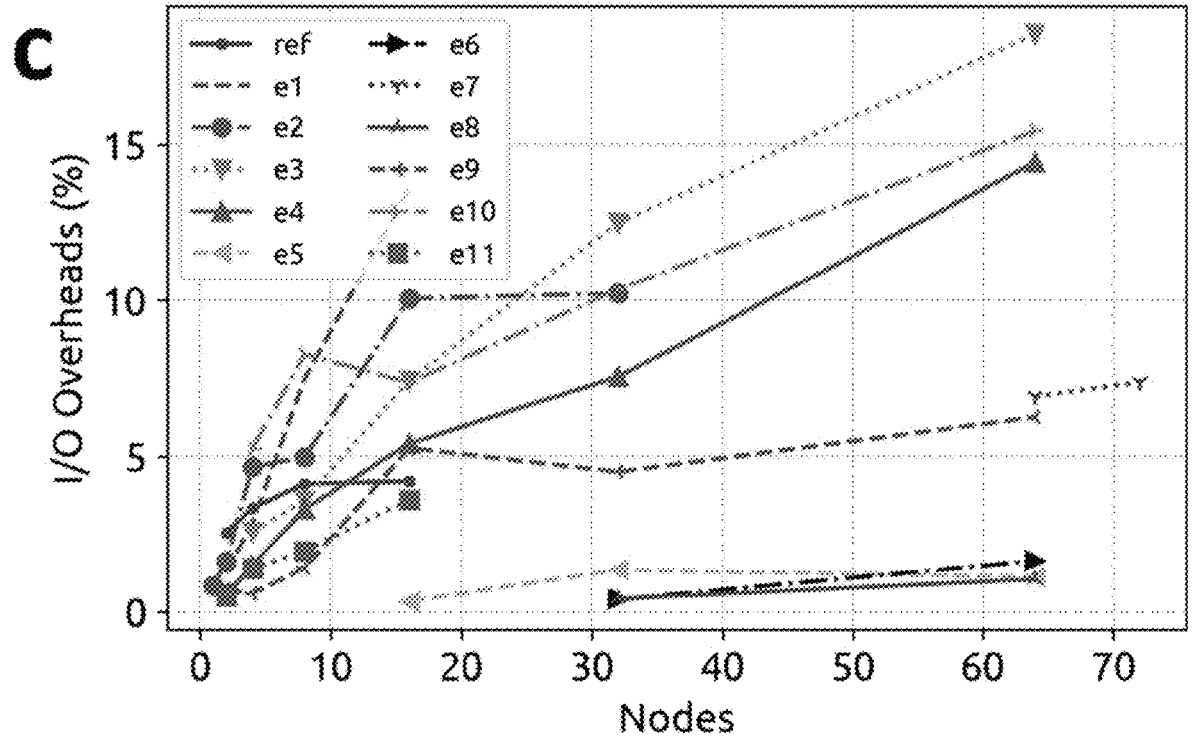
Figure 4D:
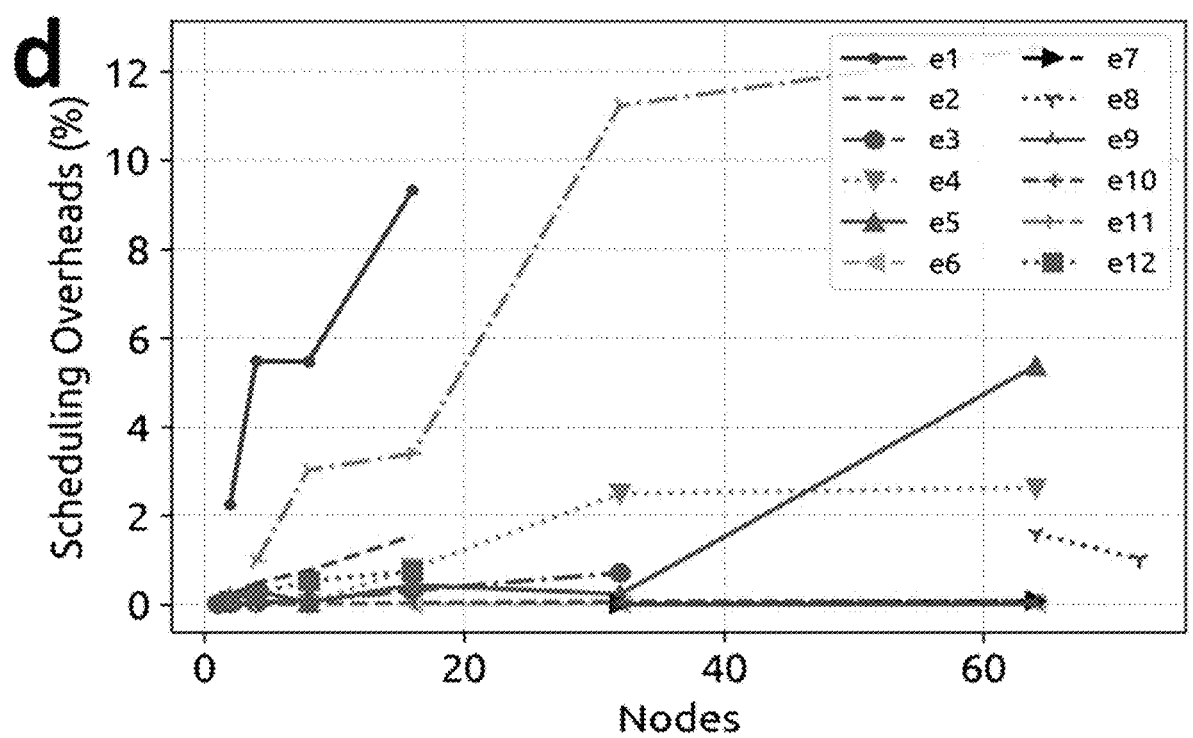
Figure 4E:
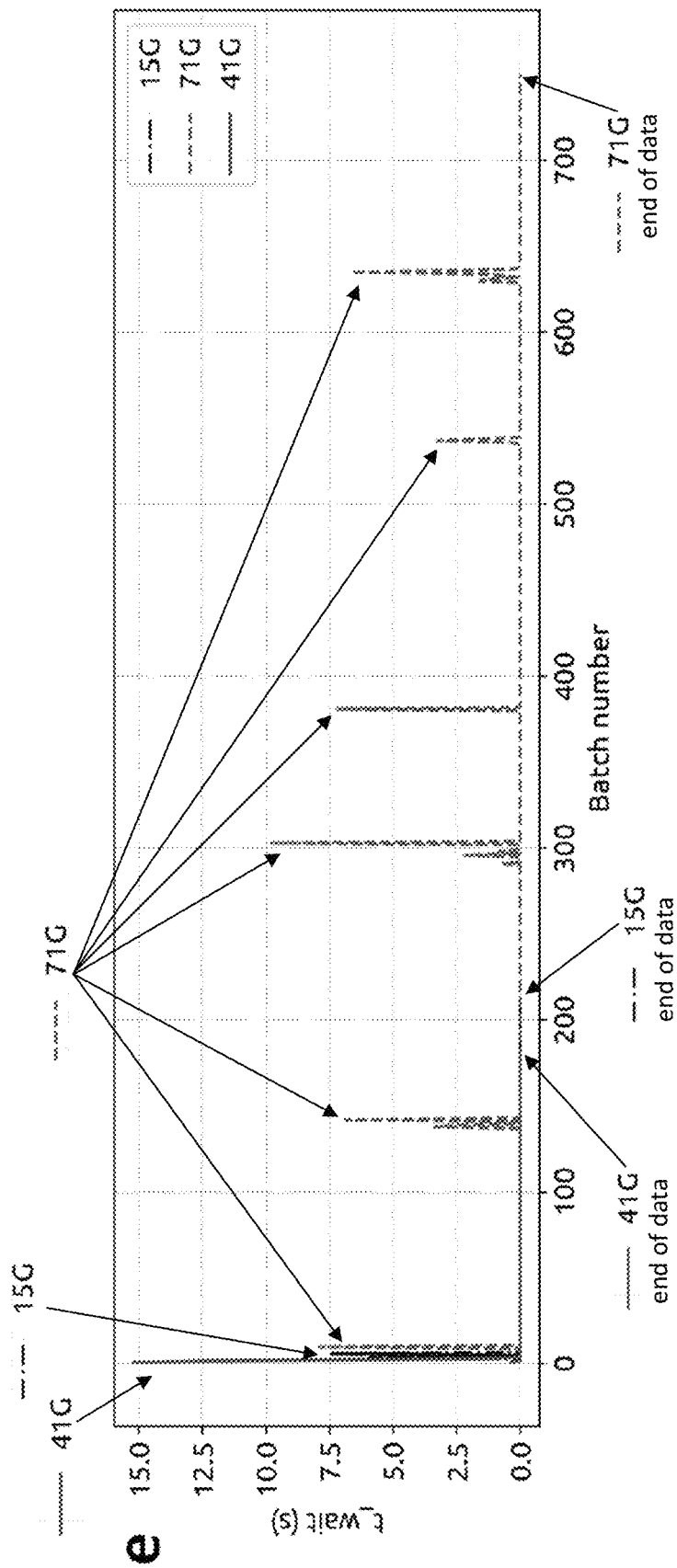

FIGS. 4A-4E are a series of performance metric charts for 12 designed experiment sets labelled e1 through e12. In FIG. 4A the load imbalance overhead costs remain under 10% in most experiment sets. In FIG. 4B the communication overhead costs remain under 5% in most experiments sets. In FIG. 4C the I/O overheads remain under 10% in most experiment sets but there is an upward trend as the number of parallel nodes increase. This occurs due to the saturation of the shared file system bandwidth. In FIG. 4D the scheduling costs remain under 5% for most experiment sets. The scheduling costs may increase if the workload per node is extremely small. In FIG. 4E the time series shows that the task scheduling algorithm efficiently redistributes the parallel threads as soon as a surge in cost is detected. The solid (red) line representing 41G (i.e., the 41 GB dataset) peaks with a t_wait value above 15 seconds (s) in the first few batches, then reduces to essentially zero or very near zero, and does not have any more data past about the 180th batch. The phantom (black) line representing 15G (i.e., the 15 GB dataset) peaks with a t_wait value just below 7.5 s in the first few batches (one or two batches later than the peak for 41G), then reduces to essentially zero or very near zero, and does not have any more data past about the 210th batch. The dashed (purple) line representing 71G (i.e., the 71 GB dataset) peaks with a t_wait value just above 7.5 s in the first few batches (one or two batches later than the peak for 15G and two to four batches later than the peak for 41G), then reduces to essentially zero or very near zero, with peaks rising above zero of (1) about 6.5 s at about batch 150, (2) just less than about 10 s at about batch 300, (3) about 7 s at about batch 375, (4) about 3 s at about batch 535, and (5) about 6.5 s at about batch 635, and has data out to about the 750th batch. Some 71G peaks occur at a single batch number (e.g., around batch 375 and around batch 535) while some 71G peaks occur across multiple nearby batch numbers (e.g., around batches 135-150, or around batches 295-301).

Figure 5:
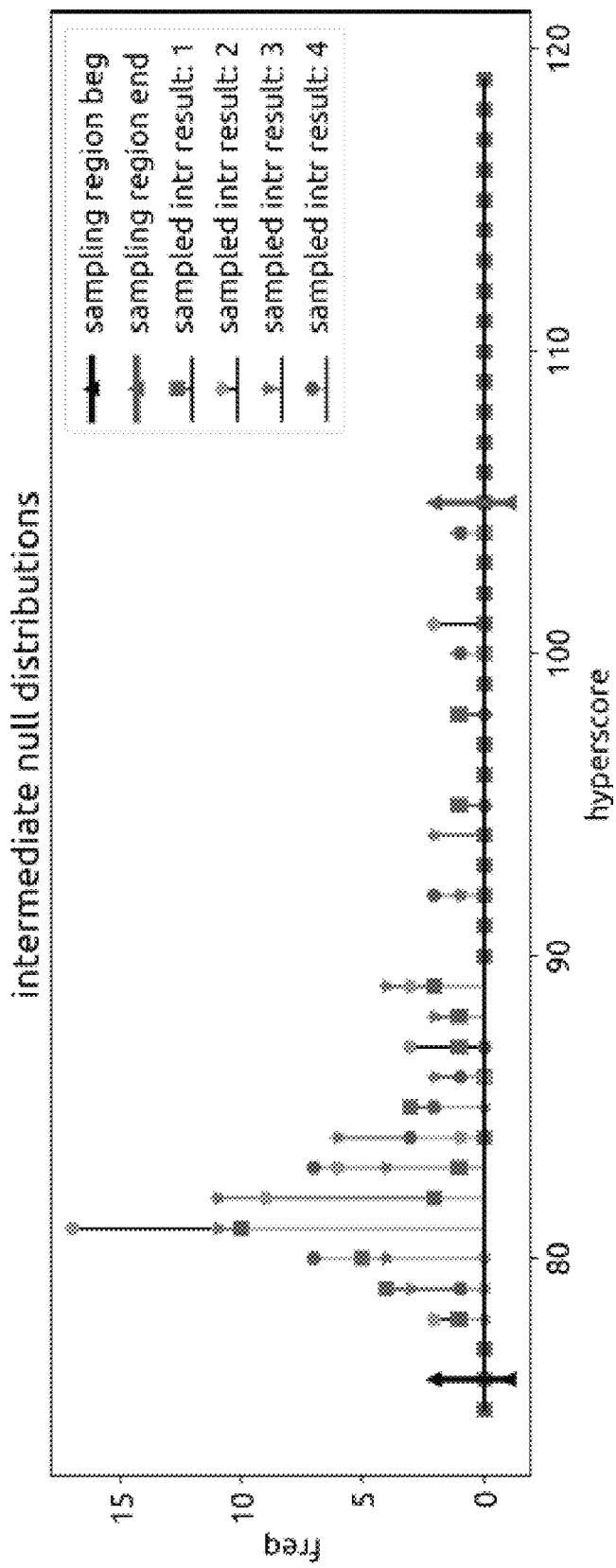
FIG. 5 is a graphical representation of sampling intermediate results around the mean.

FIG. 5 is a graphical representation of sampling intermediate results around the mean. As shown in FIG. 5 the intermediate results at all parallel processes are sampled around the mean. The mean is computed roughly by averaging the locations of three most intense samples in the distribution. Then, the most intense s=120 data points around the mean are kept around the mean and the others are discarded. The discarding method prunes the distribution tail samples first as they can be recovered by fitting a log-Weibull distribution in the sampled data.

Figure 6:
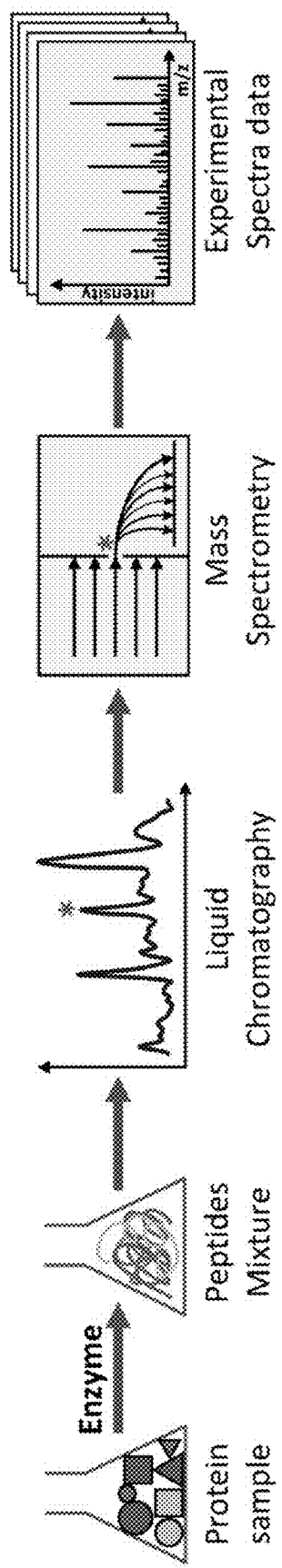
FIG. 6 is a schematic representation of a process to create experimental spectra data.
Figure 7:
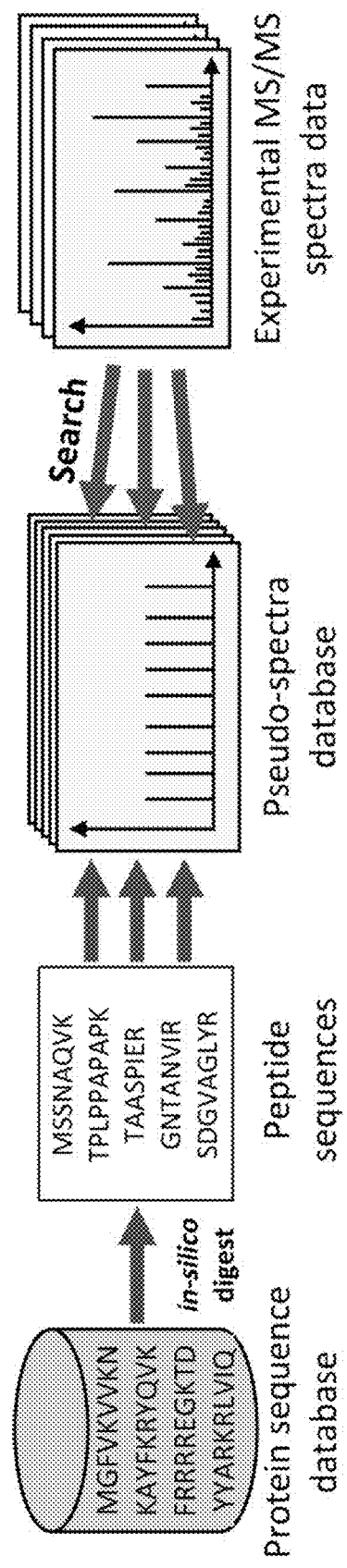
FIG. 7 is a schematic representation of a process to extract experimental spectra data from a pseudo-spectra database derived from in-silico simulation of digestion of entries from a protein sequence database by peptide sequences.

FIG. 6 is a schematic representation of a process to create experimental spectra data. The proteins are proteolyzed into peptides using an enzyme, typically Trypsin. The resultant peptide mixture is fed to an automated liquid chromatography (LC) coupled two-staged MS/MS pipeline (LC-MS/MS) which yields the experimental MS/MS data.

FIG. 7 is a schematic representation of a process to extract experimental spectra data from a pseudo-spectra database derived from in-silico simulation of digestion of entries from a protein sequence database by peptide sequences. The acquired experimental MS/MS data are compared against a database of model-spectra data. The model-spectra are simulated in-silico using a protein sequence database. Post-translational modifications (PTMs) are added in the simulation process to expand the search space.

Figure 8:
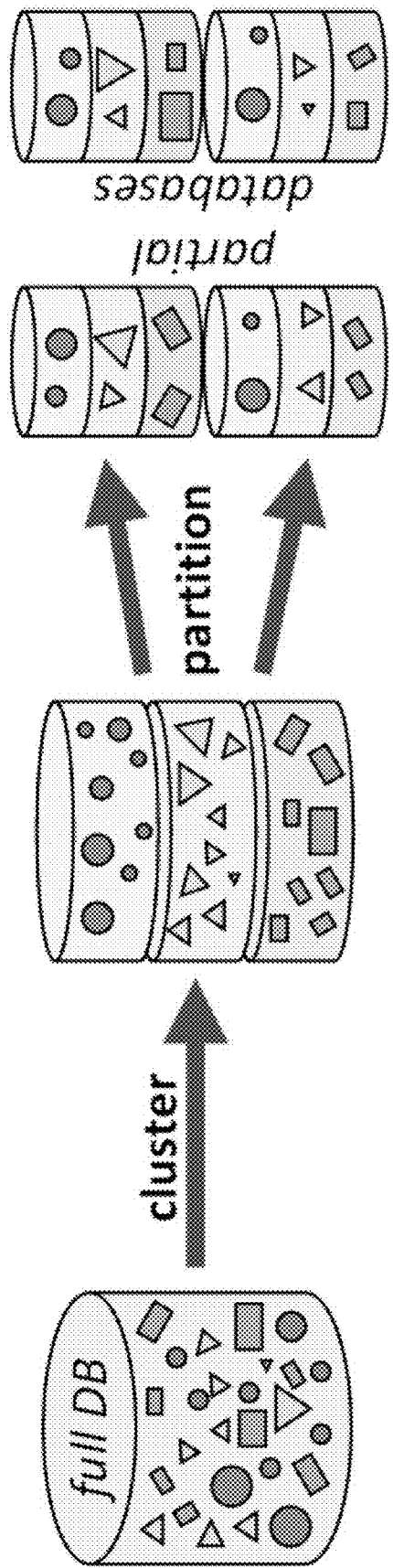
FIG. 8 is a schematic representation of improved LBE method used in the superstep 1, which clusters the model-spectra database entries (shown as shapes) using two distance metrics: Edit Distance ($\Delta e$) and Mod Distance ($\Delta m$) (Example 4).
Figure 9A:
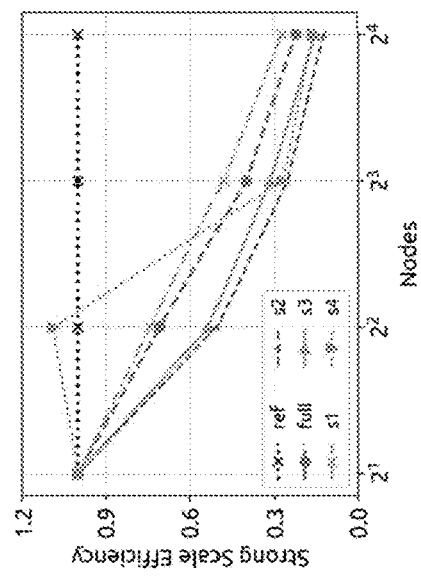
FIGS. 9A-9L are graphical representations of performance metrics (time, speed improvement, and strong scale efficiency) for experiment sets e1 through e12.
Figure 9A:
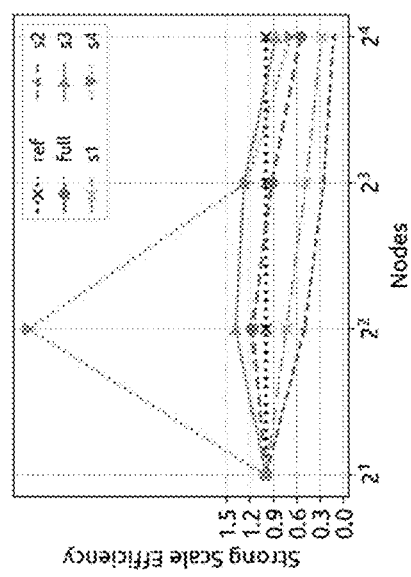
Figure 9A:
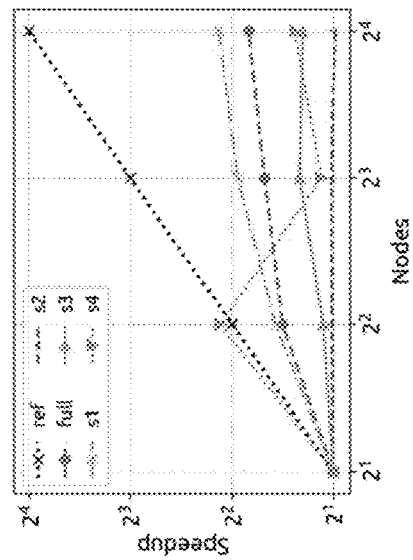
Figure 9A:
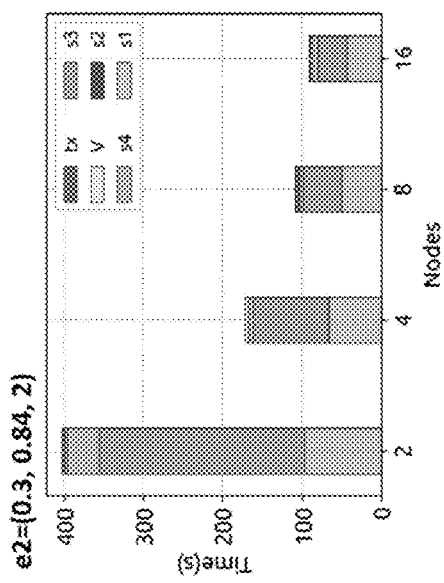
Figure 9B:
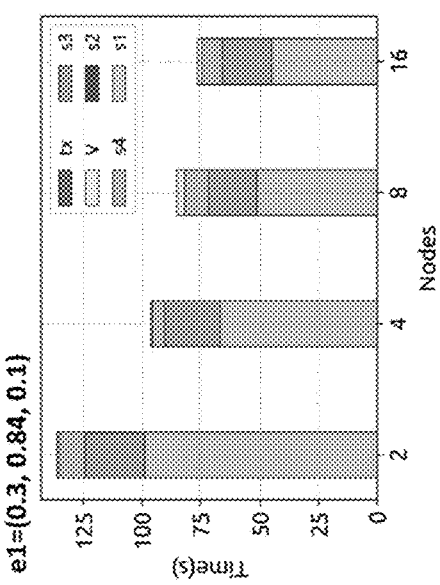
Figure 9C:
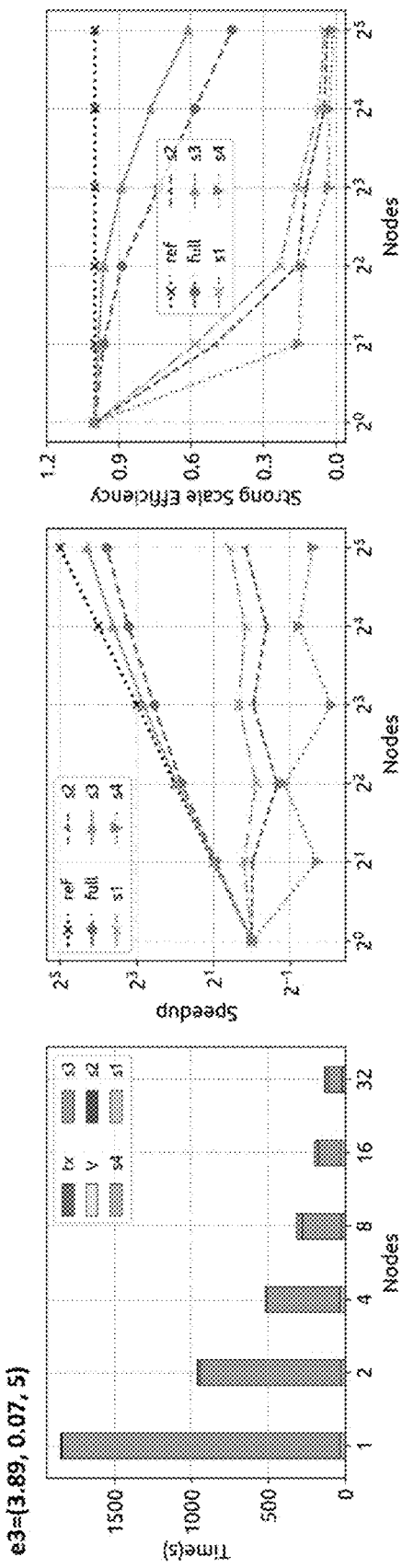
Figure 9D:
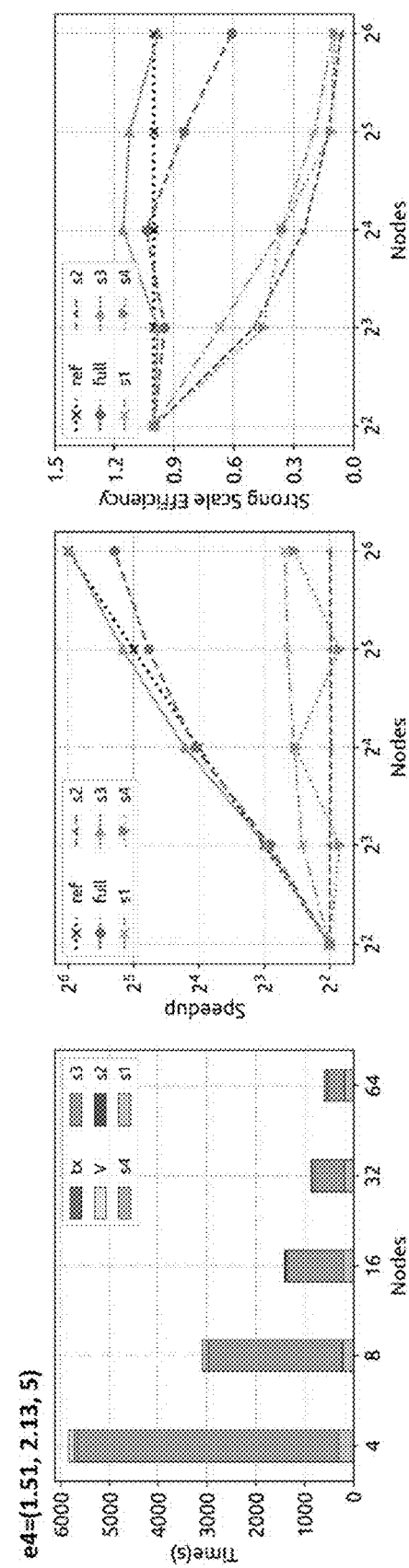
Figure 9E:
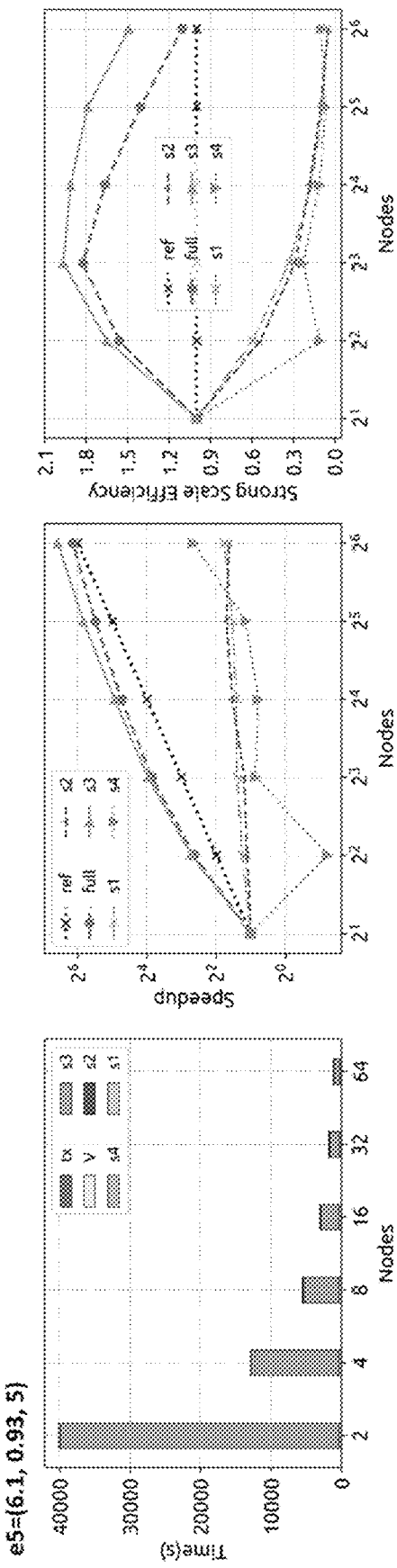
Figure 9F:
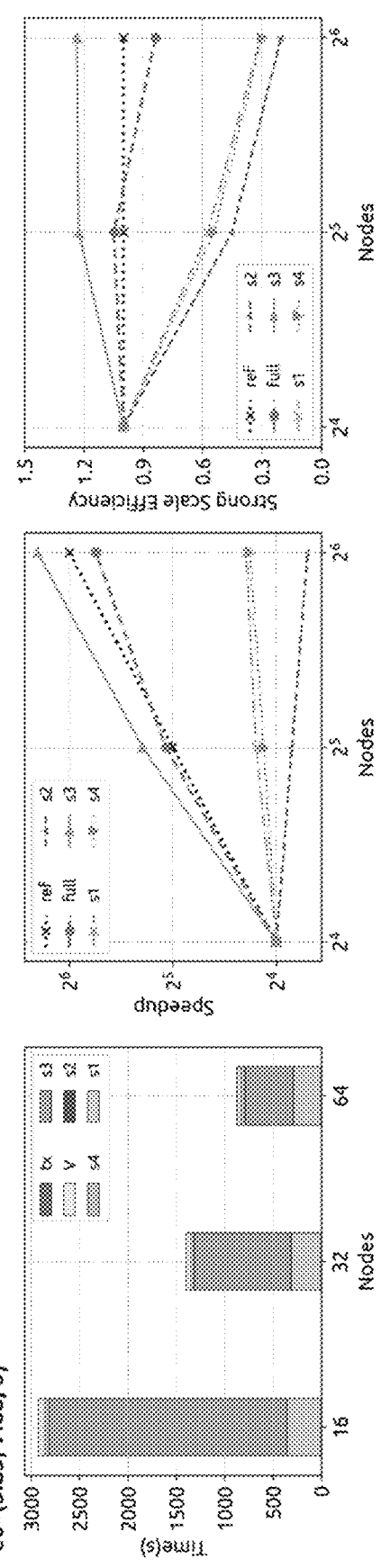
Figure 9G:
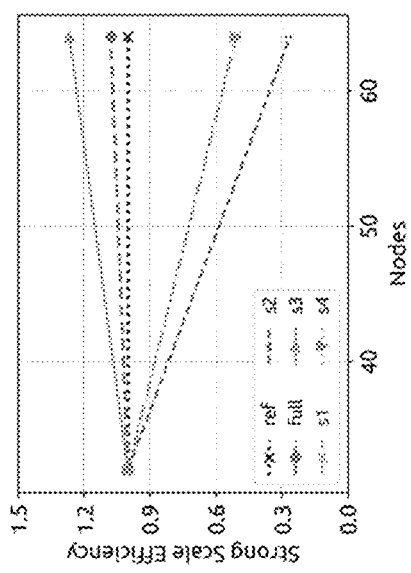
Figure 9G:
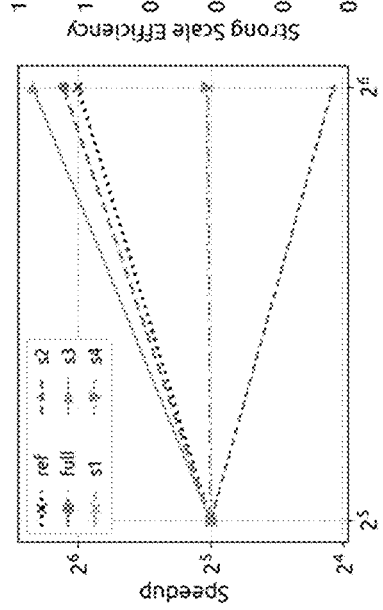
Figure 9G:
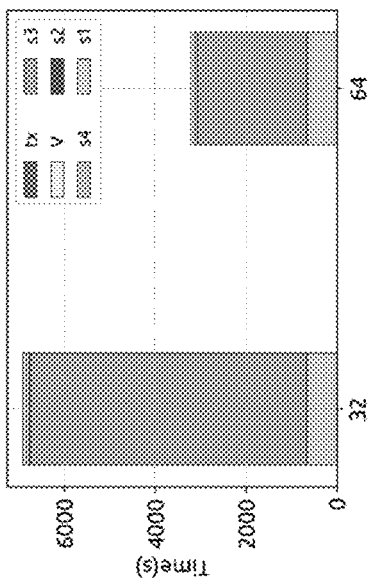
Figure 9H:
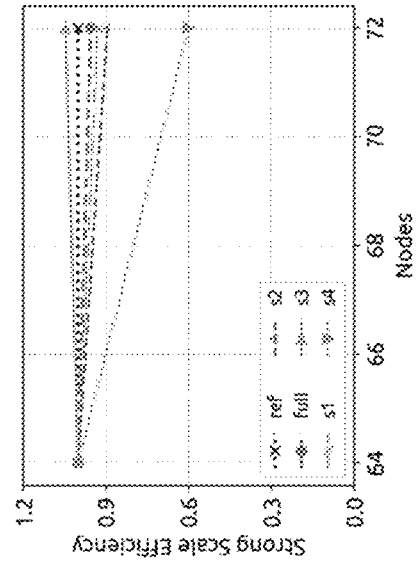
Figure 9H:
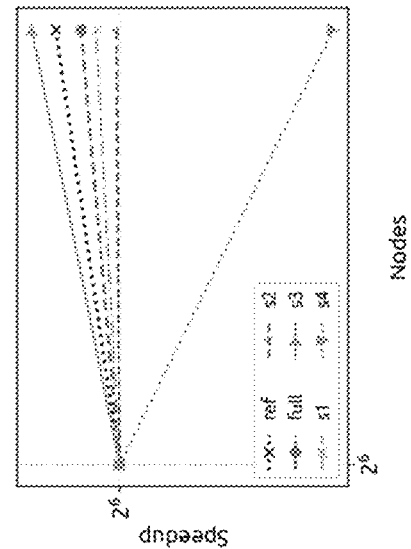
Figure 9H:
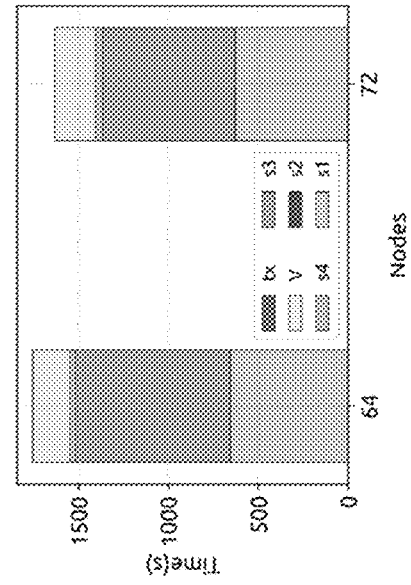
Figure 9I:
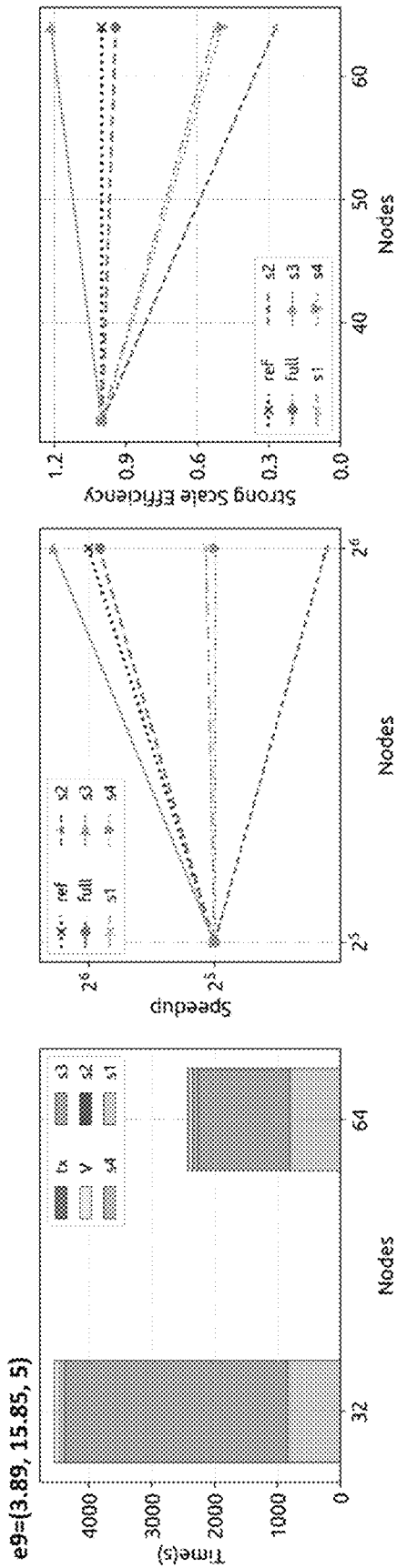
Figure 9J:
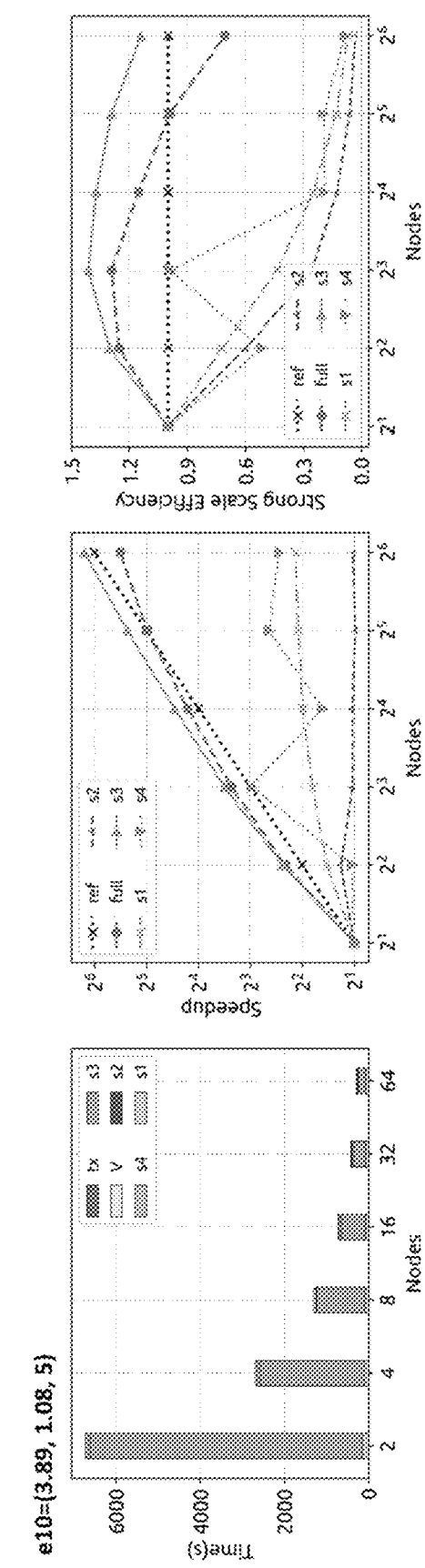
Figure 9K:
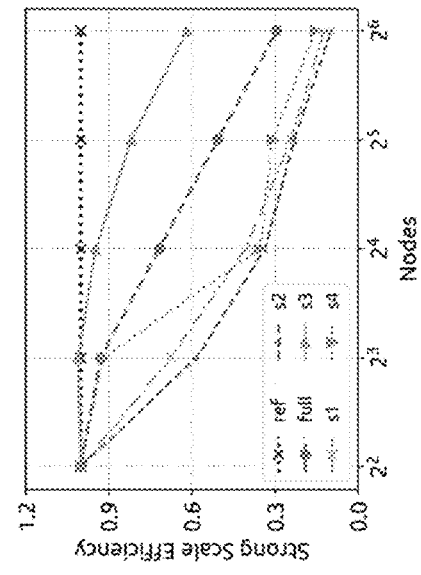
Figure 9K:
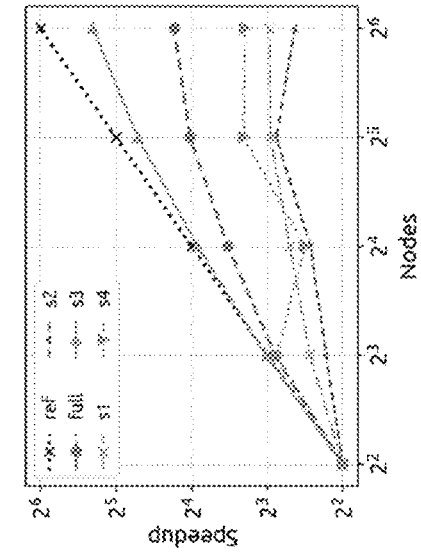
Figure 9K:
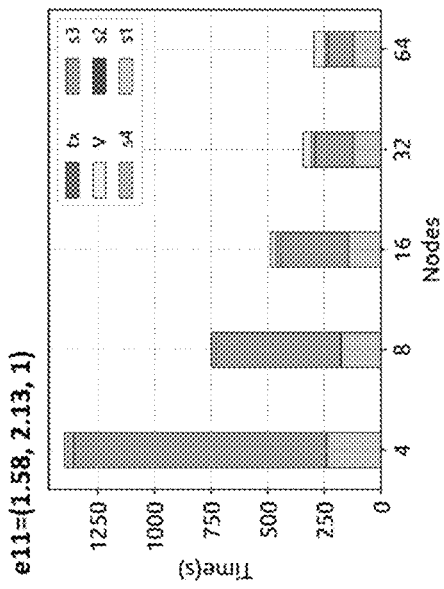
Figure 9L:
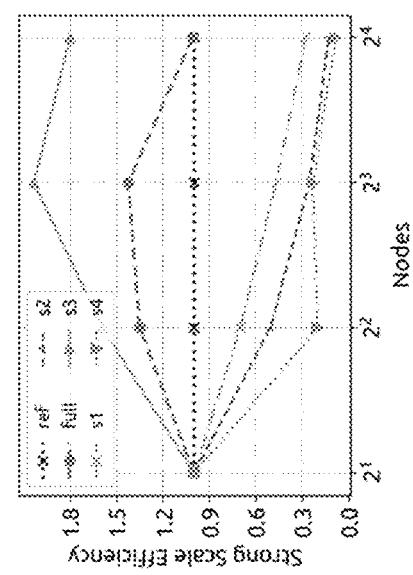
Figure 9L:
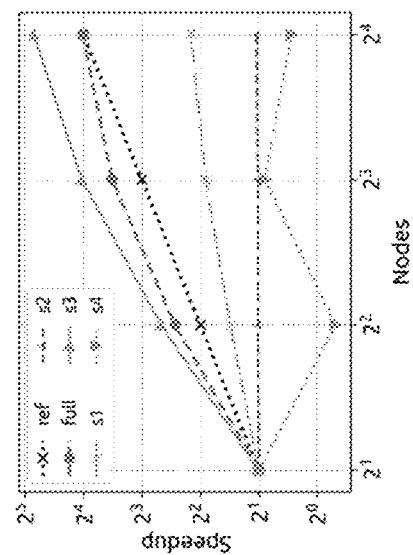
Figure 9L:
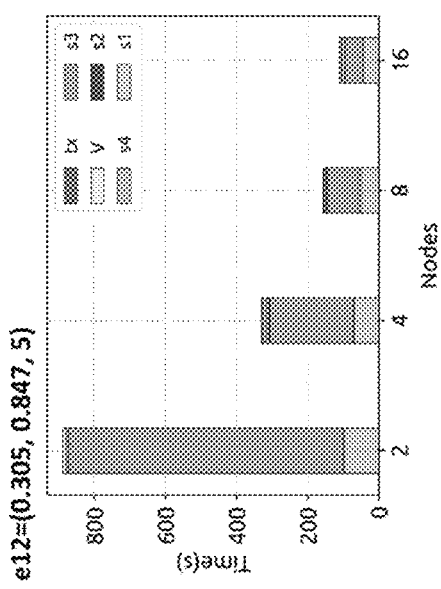

FIG. 8 is a schematic representation of improved LBE method used in the superstep 1, which clusters the model-spectra database entries (shown as shapes) using two distance metrics: Edit Distance ($\Delta e$) and Mod Distance ($\Delta m$) (Example 4). The obtained database clusters are then finely and evenly scattered across database partitions at parallel HiCOPS processes in either round robin or random fashion. The LBE method (Haseeb, 2019) is improved herein by using an additional metric called Mod Distance as described throughout this application.

FIGS. 9A-9L are graphical representations of performance metrics (time, speed improvement, and strong scale efficiency) for experiment sets e1 through e12. The following sub-figures show the decomposition of the runtime, improvement in speed ("speedup"), and strong-scale efficiency results obtained for all 12 experiment sets (e1-e12) into individual supersteps (sj) and overheads (V). The sub-figures depict that the overall efficiency increases as the workload (database, dataset and search filter) size increase. It can also be seen that the overall speedup (and efficiency) closely follows the superstep 3 (s3) confirming its largest contribution towards the overall performance. This observation further indicates that the overheads associated with these supersteps must be correctly identified and optimized for the best performance. The super-linear improvements in speed were observed in cases of large experimental workloads (e.g., database is larger than 50 million peptides and dataset is larger than 1 million spectra for select embodiments) result from the improved CPU utilization due to the reduced memory intensity per parallel node (See FIG. 3C). The definition of a large workload in this context depends on multiple factors that may change from case to case. In general, the bigger the better, in the sense that embodiments of the subject invention are much more robust and resilient against performance delays as compared to related and/or known methods.

Online Methods

Notations and Symbols

Denote the number of peptide sequences in the database as ($\zeta$), average number of post-translational modifications (PTMs) per pep-tide sequence as (m), the total database size as ($\zeta(2^m)$=D), the number of parallel nodes/processes as (P), number of cores per parallel process as (cpi), size of experimental MS/MS dataset (i.e. number of experimental/query spectra) as (q), average length of query spectrum as ($\beta$), and the total dataset size as (q$\beta$). The runtime of executing the superstep (j) by parallel task (pi) will be denoted as (Tj,pi) and the generic overheads due to boilerplate code, OS delays, memory allocation etc. will be captured via (ypi).

Runtime Cost Model

Because the HiCOPS parallel processes run in SPMD fashion, the cost analysis for any parallel process (with variable input size) is applicable for the entire system. Also, the runtime cost for a parallel process (pi∈P) to execute superstep (j) can be modeled by only its local input size (i.e. database and dataset sizes) and available resources (i.e. number of cores, memory bandwidth). The parallel processes may execute the algorithmic work in a data parallel, task parallel or a hybrid task and data parallel model. As an example, the execution runtime (cost) for a parallel process pi to execute superstep (j) which first generates D model-spectra using algorithm $k_1$ and then sorts them using algorithm $k_2$ in data parallel fashion (using all cpi cores) will be given as follows:

$$T_{j,p_i} = k_{j1}(D) + k_{j2}(D) + \gamma_{p_i} \quad (2)$$

Similarly, if the above steps $k_z$ are performed in a hybrid task and data parallel fashion, the number of cores allocated to each ($k'_{jz}$) must also be considered. For instance, in the above example, if the two algorithmic steps are executed in sub-task parallel fashion with $c_{pi}/2$ cores each, the execution time will be given as:

$$T_{j,p_i} = \max(k_{j1}(D, c_{p_z}/2), k_{j2}(D, c_{p_z}/2)) + \gamma_{p_i} \quad (3)$$

For analysis, if the time complexity of the algorithms used for step $k_{jz}$ is known (say O(.)), convert it into a linear function $k'_{jz}$ with its input data size multiplied by its runtime complexity. This conversion will allow better quantification of serial and parallel runtime portions as seen in later sections. As an example, if it is known that the sorting algorithms used for $k_{j2}$ have time complexity: O(N log N), the equation 2 can be modified to:

$$T_{j,p_i} = k_{j1}(D) + k'_{j2}(D \log D) + \gamma_{p_i} \quad (4)$$

Remarks: The formulated model will be used to analyze the runtime cost for each superstep, quantify the serial, parallel and overhead costs in the overall design, and optimize the overheads.

Superstep 1: Partial Database Construction

In this superstep, the HiCOPS parallel processes construct a partial database by executing the following three algorithmic steps in data parallel fashion (FIG. 2):

1. Generate the whole peptide database and extract a (load balanced) partition.
2. Generate the model-spectra data from the local peptide database partition.
3. Index the local peptide and model-spectra databases (fragment-ion index).

The database entries are generated and partitioned through the LBE algorithm (Haseeb, supra.), supplemented with a new distance metric called Mod Distance ($\Delta$m). The proposed $\Delta$m separates the pairs of database entries based on the edit locations if they have the same Edit Distance ($\Delta$e) (See Example 3). The reason for supplementing LBE with the new distance metric is to better construct computationally-near-identical (load balanced) database partitions across parallel HiCOPS processes. Embodiments partition large databases into small but evenly-distributed partitions which are processed on parallel nodes (e.g., the data in each partition would roughly look similar from a processing resources perspective). Mod Distance is an improvement implemented in the LBE algorithm which works in conjunction with the Edit Distance. The primary role of Mod Distance is to act as a tie-breaker in case Edit Distance is not sufficient to parse the data into equally balanced partitions. Mod Distance improves the efficiency of load balancing.

FIG. 8 illustrates the generic LBE algorithm, a novel technique for efficient model-spectra database partitioning. For a pair of peptide database entries (x, y), assuming the sum of unedited letters from both sequence termini is (a), the Mod Distance ($\Delta$m) is given as:

$$\Delta m(x, y) = 2 - \frac{a}{\max(len(x), len(y))}$$

Cost Analysis: The first step generates the entire database of size (D) and extracts a partition (of roughly the size $D/P = D_{pi}$) in runtime: $k_{11}(D)$. The second step generates the model-spectra from the partitioned database using standard algorithms (see, e.g., Eng et al., An approach to correlate tandem mass spectral data of peptides with amino acid sequences in a protein database, Journal of the American Society for Mass Spectrometry, 5(11):976-989, 1994, which is hereby incorporated by reference herein in its entirety), in runtime: $k_{12}(D_{pi})$. The third step constructs a fragment-ion index (e.g., similar to Kong et al., Msfragger: ultrafast and comprehensive peptide identification in mass spectrometry-based proteomics, Nature methods, 14(5):513, 2017; Chi et al., pfind-alioth: A novel unrestricted database search algorithm to improve the interpretation of high-resolution MS/MS data, Journal of proteomics, 125:89-97, 2015; and Haseeb et al., Efficient shared peak counting in database peptide search using compact data structure for fragment-ion index, 2019 IEEE International Conference on Bioinformatics and Biomedicine (BIBM), pages 275-278. IEEE, 2019, which are hereby incorporated by reference herein in their respective entireties), in runtime: O(N log N). The CFIR-Index (Haseeb et al., Efficient shared peak counting in database peptide search using compact data structure for fragment-ion index, 2019 IEEE International Conference on Bioinformatics and Biomedicine (BIBM), pages 275-278. IEEE, 2019) indexing method was employed due to its smaller memory footprint. This results in time $k'_{13}(D_{pi} \log D_{pi})$ for the indexing step. Collectively, the runtime for this superstep is given by Equation 5.

$$T_1 = \max_{p_i}(k_{11}(D) + k_{12}(D_{p_i}) + k'_{13}(D_{p_i} \log D_{p_i})) + \gamma_{p_i} \quad (5)$$

Remarks: Equation 5 depicts that the serial part of execution time i.e. $k_{11}(D)$ limits the parallel efficiency of superstep 1. However, using simpler but faster database partitioning may result in imbalanced partial databases leading to severe performance deprecation.

Superstep 2: Experimental MS/MS Data Pre-Processing

In this superstep, the HiCOPS parallel processes pre-process a partition of experimental MS/MS spectra data by executing the following three algorithmic steps in data parallel fashion (e.g., as shown in FIG. 2):

1. Read the dataset files, create a batch index and initialize internal structures.
2. Pre-process (i.e. normalize, clear noise, reconstruct etc.) a partition of experimental MS/MS data.
3. Write-back the pre-processed data.

The experimental spectra are split into batches such that a reasonable parallel granularity is achieved when these batches are searched against the database. By default, the maximum batch size is set to 10,000 spectra and the minimum number of batches per dataset is set to P. The batch information is indexed using a queue and a pointer stack to allow quick access to the pre-processed experimental data in the superstep 3.

Cost Analysis: The first step reads the entire dataset (size: $q\beta$) and creates a batch index in runtime: $k_{21}(q\beta)$. The second step may pre-process a partition of the dataset (of roughly the size: $q\beta/P=Qpi$) using a data pre-processing algorithm (e.g., Ding et al., A novel approach to denoising ion trap tandem mass spectra, Proteome Science, 7(1):9, 2009; Deng et al., pclean: an algorithm to preprocess high-resolution tandem mass spectra for database searching, Journal of proteome research, 18(9):3235-3244, 2019; and Liu et al., Full-spectrum prediction of peptides tandem mass spectra using deep neural network, Analytical Chemistry, 92(6):4275-4283, 2020, which are hereby incorporated by reference herein in their respective entireties), in runtime: $k_{22}(Qpi)$. The third step may write the pre-processed data back to the file system in runtime: $k_{23}(Qpi)$. The second and third steps may altogether be skipped in subsequent runs or in case when the pre-processed spectra data are available. Collectively, the runtime for this superstep is given by Equation 6.

$$T_2 = \max_{p_i}(k_{21}(q\beta) + k_{22}(Q_{p_i}) + k_{23}(Q_{p_i}) + \gamma_{p_i}) \quad (6)$$

Remarks: Equation 6 depicts that the parallel efficiency of superstep 2 is highly limited by its dominant serial portion i.e. $k_{21}(q\beta)$. Moreover, this superstep is sensitive to the file system bandwidth since large volumes of data may need to be read from and written to the shared file system.

Superstep 3: Partial Database Peptide Search

This superstep in HiCOPS workflow may be responsible for 80-90% of the database peptide search algorithmic workload in real world experiments. In this superstep, the HiCOPS parallel processes search the pre-processed experimental spectra against their partial databases by executing the following three algorithmic steps in a hybrid task and data parallel fashion (FIG. 2):

1. Load the pre-processed experimental MS/MS data batches into memory.
2. Search the loaded spectra batches against the (local) partial database and pro-duce intermediate results.
3. Serialize and write the intermediate results to the shared file system assigning them unique tags.

Cost Analysis: The sub-task (R) reads the experimental data batches in runtime: $k_{30}(q\beta)$. The sub-task (I) iteratively filters the partial database using multiple criteria followed by formal spectral comparisons (or scoring). Most commonly, the database peptide search algorithms use two or three database filtration steps such as peptide precursor mass tolerance, shared fragment-ions, and sequence tags. Embodiments may use the first two filtration methods (e.g., peptide precursor mass tolerance, shared fragment-ions, or sequence tags) that execute in run-time: $k_{31}(qDpi) + k_{32}(q\beta\alpha pi)$ respectively, or other methods known in the art. Here, the api represents the average filtered database size filtered from the first step. The formal experimental spectrum to model-spectra comparisons (spectral comparisons) are performed using scoring methods such as cross-correlation, hyperscore, or other scoring methods known in the art, in runtime: $k_{33}(q\beta\sigma pi) + k_{34}(q\mu pi)$. Here, the σpi and μpi represent the average number of filtered shared-ions and model-spectra per experimental spectrum. Finally, the sub-task K writes the partial results to the shared file system in runtime: $k_{35}(q)$.

Overhead Costs: Multiple runtime overheads stemming from load imbalance, producer-consumer speed mismatch, file system bandwidth congestion can affect the performance of this superstep. Therefore, it is important to capture them using an additional runtime cost: Vpi (q, Dpi, P). The optimizations implemented to alleviate these overhead costs in superstep 3 include buffering, task scheduling, load balancing and data sampling (discussed in later sections). Collectively, the runtime for this superstep is given by Equation 10.

The runtime of sub-task R. i.e. $t_{p_i}(r, |r|)$, is given as:

$$t_{p_i}(r,|r|) = k_{30}(q\beta,|r|) \quad (7)$$

The runtime of sub-task I, i.e. $t_{p_i}(i, |i|)$, is given as:

$$t_{p_i}(i,|i|) = k_{31}(qD_{p_i'}|r|) + k_{32}(q\beta\alpha_{p_i'}|i|) + k_{33}(q\beta\sigma_{p_i'}) + k_{34}(q\mu_{p_i'}|i|)$$

Or:

$$t_{p_i}(i,|i|) = k'_{31}(q\log(D_{p_i}),|i|) + k'_{32}(q\beta\log(\alpha_{p_i}),|i|) + k_{33}(q\beta\sigma_{p_i'}|i|) + k_{34}(q\mu_{p_i'}|i|) \quad (8)$$

The runtime of sub-task K, i.e. $t_{p_i}(k, |k|)$, is given as:

$$t_{p_i}(k,|k|) = k_{35}(q,|k|) \quad (9)$$

Combining equations 7, 8 and 9 we have:

$$T_3 = \max_{p_i}(\max(t_{p_i}(r,|r|), t_{p_i}(i,|i|), t_{p_i}(k,|k|))) + V_{p_i}(q, D_{p_i'}P) + \gamma_{p_i} \quad (10)$$

Remarks: Equations 7, 8, 9 and 10 depict that the parallel runtime portion of this superstep grows quadratically superseding the (small) serial portions capable of near ideal parallel efficiency if the overheads are eliminated.

Superstep 4: Result Assembly

In this superstep, the HiCOPS parallel processes assemble the intermediate results from the last superstep into complete results by executing the following algorithmic steps in a hybrid task and data parallel fashion (FIG. 1, panel d):

1. Read a set of intermediate result batches, assemble them into complete results, and send the assembled results to their parent processes.
2. Receive complete results from other parallel processes and synchronize communication.
3. Write the complete results to the file system.

Two parallel sub-tasks are created to execute the algorithmic steps in this super-step. The first sub-task reads sets of intermediate results from the shared file system (or shared memory) (satisfying: tag % $p_i=0$; $p_i \in$ MPI de-serializes them and assembles the complete results. The statistical significance scores are then computed and sent to their origin processes. For example, the process with MPI rank 4 will process the all intermediate result batches with tag 0×8 i where i=0, 1, . . . , P−1. The assembly process is done through signal addition and shift operations illustrated in FIG. 1D. The expectation scores (e-Values (ev)) are computed using null hypothesis approach by first smoothing the assembled data through Savitzky-Golay filter (or other filters known in the art) and then applying significance test through either the Linear-Tail Fit or log-Weibull (Gum-bel) Fit method illustrated in FIG. 1D, or other methods known in the art. Some curve smoothing/fitting methods provide more accurate results at higher computing cost, others have lesser accuracy but can be used at a lower computing cost. The computed e-Values along with additional information (16 bytes) are sent to the HiCOPS process that recorded the most significant database hit (origin). The computed results are not sent immediately but are accumulated in a map data structure as part of the first parallel sub-task and sent collectively to the second parallel sub-task when all batches are done. All available cores (cpi) are assigned to this sub-task. Algorithm 4 depicts the algorithmic work performed by this sub-task.

The second sub-task runs and waits for P−1 packets of complete data from other HiCOPS processes. This task runs inside an extra (over-subscribed) thread in a con-current fashion and only activates when incoming data is detected. Finally, once the two sub-tasks complete (join), the complete results are written to the file system in data parallel fashion using all available threads.

Cost Analysis: The first sub-task reads the intermediate results, performs regression and sends computed results to other processes in runtime: $k_{41}(Q_{pi}, c_{pi}) + k_{42}(Q_{pi}, c_{pi}) + k_{43}(P, 1)$ time. The second sub-task receives complete results from other tasks in runtime: $k_{44}(P, 1)$. Finally, the complete results are written in runtime: $k_{45}(Q_{pi})$. Collectively, the runtime for this superstep is given by equation 11.

$$T_4 = \max_{P_i}(\max(k_{41}(Q_{P_i}c_{P_i}) + k_{42}(Q_{P_i}c_{P_i}) + k_{43}(P,1) + k_{44}(P,1) + k_{45}(Q_{P_i}) + \gamma_{P_i}) \quad (11)$$

To simplify equation 11, re-write it as a sum of computation costs plus the communication overheads ($k_{com}(P, 1)$) as:

$$T_4 = \max_{P_i}(k_{41}(Q_{P_i}c_{P_i}) + k_{42}(Q_{P_i}c_{P_i}) + k_{com}(P,1) + k_{45}(Q_{P_i}) + \gamma_{P_i}) \quad (12)$$

Assuming that the network latency is denoted as (ω), bandwidth is denoted as (π)

$$k_{com}(P,1) \approx 2(P-1)(\omega + 16Q_{pdi}/\pi)$$

Remarks: As the communication per process are limited to only one data exchange between any pair of processes, the overall runtime given by equation 12 is highly scalable. The effective communication cost depends on the amount of overlap with computations and the network parameters at the time of experiment.

Performance Analysis

To quantify the parallel performance, decompose the total HiCOPS time $T_H$ (Eq. 1) into three runtime components. i.e. parallel runtime ($T_p$), serial runtime ($T_s$) and overheads runtime ($T_o$) given ns:

$$T_H = \sum_{j=1}^{4} \max_{P_i}(T_j, p_i) = T_o + T_s + T_p \quad (13)$$

Using equations 1, 5, 6, 10, and 12, we separate the three runtime components as:

$$T_o = V_{P_i}(q, D_{P_i}, P) + \gamma_{P_i} \quad (14)$$

$$T_s = k_{11}(d) + k_{21}(q\beta) + k_{com}(P,1) \quad (15)$$

and:

$$T_p = k_{12}(D_{P_i}) + k'_{12}(D_{P_i} \log D_{P_i}) + k_{22}(Q_{P_i}) + k_{23}(Q_{P_i}) +$$

$$\max(t_{p_i}(t,|r|), t_{p_i}(i,|i|), t_{p_i}(k,|k|)) + k_{41}(Q_{P_i}c_{P_i}) +$$

$$k_{42}(Q_{P_i}c_{P_i}) + k_{45}(Q_{P_i}) \quad (16)$$

$T_B$ is the minimum serial time required for HiCOPS execution and cannot be further reduced. Therefore, we will focus on optimizing the remaining runtime: $T_F = T_p + T_o$.

Using equations 14 and 16 we have:

$$T_F = k_{12}(D_{P_i}) + k'_{12}(D_{P_i} \log D_{P_i}) + k_{22}(Q_{P_i}) + k_{23}(Q_{P_i}) +$$

$$\max(t_{p_i}(t,|r|), t_{p_i}(i,|i|), t_{p_i}(k,|k|)) + k_{41}(Q_{P_i}c_{P_i}) +$$

$$k_{42}(Q_{P_i}c_{P_i}) + k_{45}(Q_{P_i}) + T_o \quad (17)$$

Since the HiCOPS parallel processes divide the database and experimental dataset roughly fairly in supersteps 1 and 2, the first four and the sixth term in $T_p$ are already almost optimized, so we can prune them from $T_F$:

$$T_F = \max(t_{p_i}(t,|r|), t_{p_i}(i,|i|), t_{p_i}(k,|k|)) + k_{41}(Q_{P_i}c_{P_i}) +$$

$$k_{42}(Q_{P_i}c_{P_i}) + +k_{45}(Q_{P_i}) + T_o \quad (18)$$

The superstep 4 runtime is optimized for maximum parallelism (and least inter-process communication) and that the superstep 3 performs the largest fraction of overall algorithmic workload. Thus, removing the superstep 4 terms from TF simplifies the analysis:

$$T_F = \max(t_{p_i}(t,|r|), t_{p_i}(i,|i|), t_{p_i}(k,|k|)) + T_o$$

The superstep 3 is executed using the producer-consumer pipeline (FIG. 1C) where the sub-task R must produce all data before it can be consumed by I meaning its runtime must also be smaller than $t_{p_i}(i, |i|)$ and $t_{p_i}(k, |k|)$ allowing a safe removal from the above equation yielding:

$$T_F = \max(t_{p_i}(i,|i|), t_{p_i}(k,|k|)) + T_o$$

In above equation, rewrite the max(.) term as the time to complete sub-task I:($t_{p_i}(i, |i|)$) plus the extra time to complete sub-task K (the last consumer): $t_x(k)$. Therefore, using equation 9:

$$T_F = k'_{31}(q \log(D_{P_i}), |i|) + k'_{32}(q\beta \log(\alpha_{P_i}), |i|) +$$

$$k_{33}(q\beta\sigma_{P_i}|i|) + k_{34}(q\mu_{P_i}|i|) + t_x(k)T_o \quad (19)$$

Prune the first two terms in the equation 19 as well since their runtime contribution: O(log 1V) will be relatively very small. Finally, using equation 14 in 19:

$$T_F = k_{33}(q\rho\sigma_{P_i}|i|) + k_{34}(q\mu_{P_i}|i|) + V_{P_i}(q, D_{P_i}, P) + \gamma_{P_i} \quad (20)$$

Remarks: The equations 17-19 and the simplifications made may be modified according to the changes in superstep design and/or the algorithms employed in either superstep.

Optimizations

The overhead cost term: $V_i(q, P)$ represents the load imbalance (or synchronization), producer-consumer speed mismatch, and data read costs, while the term: $t_x(k)$ represents the data write cost. These overheads may result in a large subset of processing cores to idle (wasted CPU cycles). Furthermore, the load imbalance cost encapsulates all other costs in itself. This is because at a macro level (when only measuring the total overhead time wasted by waiting for one or more lagging processes) the total cost is actually also the load imbalance cost. The total cost (or now the load imbalance cost) may itself consist of many factors including the I/O, tx(k), memory, etc., as explained above.

The following sections discuss the optimization techniques employed to alleviate these overhead costs.

Bu☐ering

Four queues, the forward queue ($q_f$), recycle queue ($q_r$) and result queues ($q|_k$, $q'_k$) are initialized and routed between the producer-consumer sub-tasks in the superstep 3 (FIG. 1C) as: R→I, R←I, I→K and I←K respectively. The $q_r$ initialized with (e.g., 20) empty buers for the sub-task R to fill the pre-processed experimental data batches and push in $q_f$. The sub-task I removes a buffer from $q_f$ consumes it (searches it) and pushes back to qr for re-use. The results are pushed to $q_k$ which are consumed by sub-task K and pushed back to $q'_k$ for re-use. Three regions are defined for the queue $q_f$ based on the number of data buffers it contains at any time. i.e. w1:($q_f$.len<5), $w_2$:(5≤$q_f$.len≤15) and $w_3$:($q_f$.len≥15). These regions ($w_1$) are used by the task-scheduling algorithm discussed in the following section.

Task Scheduling

The task scheduling algorithm is used to maintain a synergy between the producer-consumer (sub-task) pipeline in the superstep 3. The algorithm initializes a thread pool of $c_{pi}+2$ threads where $c_{pi}$ is the number of available cores. In the first iteration, 2 threads are assigned to the sub-tasks R and K while the remaining $c_{pi}-2$ threads are assigned to sub-task I. Then, in each iteration, the $q_f$ region: $w_1$, and the $q_f$.pop( ) time for I, given by: twait, are monitored. A time series is built to forecast the next twait (i.e. $t_{fct}$) using double exponential smoothing or other methods known in the art. The $t_{wait}$ is also accumulated into $t_{cum}$. Two thresholds are defined: minimum wait ($t_{min}$) and maximum cumulative wait ($t_{max}$). Using all this information, a thread is removed from sub-task I and added to R if the following conditions are satisfied:

$$c_{I \to R} = (t_{wait} \geq t_{min} \wedge (t_{cum} + t_{fct}) > t_{max}) \vee (w_1 = w_1 \wedge |r| = 0)$$

The $t_{cum}$ is set to 0 every time a thread is added to R. Similarly, a thread is removed from sub-task R and added to I if the following conditions are satisfied.

All threads are removed from R if the queue $q_f$ becomes full or there is no more experimental MS/MS data left to be loaded.

$$c_{R \to I} = (w_1 = w_3 \wedge |r| > 1) \vee q_f.\text{full}(\ )$$

The sub-task K uses its 2 over-subscribed threads to perform the overlapped I/O operations concurrently (FIG. 1C).

Load Balancing

The algorithmic workload in equation 20 is given by: $k_{33}(q^{\beta\sigma}_{pi}, |i|) + k_{34}(q^{\mu}_{pi}, |i|)$. Here, the terms qβ and q are constants (experimental data size) whereas the terms $\sigma_{pi}$ and $\mu_{pi}$ are variable. The variable terms represent the filtered database size for a parallel HiCOPS process ($p_i$) and thus, must be balanced across processes. This may be accomplished statically by constructing balanced database partitions (hence a balanced workload) using the LBE algorithm supplemented with the Mod Distance metric in Superstep 1 (Online Methods, FIGS. 1A and 8). The correctness of the LBE algorithm for load balancing is proven in Example 4.

Sampling

The intermediate result produced by a parallel process ($p_i$) for an experimental spectrum (q) included: M top scoring database hits (8 bytes) and the frequency distribution of scores (local null distribution) (2048 bytes). Since this frequency distribution follows a log-Weibull, most of the data are localized near the mean. Using this information, locate the mean and sample a number, s (e.g., s=120) most intense samples from the distribution, and remove the samples, if necessary, from the tail first. This allows to fit all the intermediate results in a buffer of 256 bytes limiting the size of each batch to 1.5 MB. Thus, the intermediate results are quickly written to the file system by the sub-task K resulting in minimum data write cost: $t_x(k)$. FIG. 5 illustrates an example of the sampling method.

Code Availability

The HiCOPS core parallel model and algorithms have been implemented using object-oriented C++14 and MPI. The rich instrumentation feature has been implemented via Timemory for performance analysis and optimizations. Timemory is a software toolkit that allows an elegant way of instrumenting code using a rich/diverse set of instrumentation metrics which can be further used to gain insights into the software performance. Timemory is not itself directly critical to HiCOPS's performance, but was used to perform a wide-ranged instrumentation to figure out when and why HiCOPS was or is performing better or worse. Command-line tools for MPI task mapping (e.g., Example 5, Algorithm 5), user parameter parsing, peptide sequence database processing, file format conversion and result post-processing can also be distributed with the HiCOPS framework. The build may be managed via CMake 3.11+, or other tools known in the art. Please refer to the software web page: hicops.github.io for source code and documentation.

Data Availability

The datasets and database used in this study are publicly available from the mentioned respective data repositories. The experiment configuration files and raw results pertinent to the findings of this study are available from the corresponding author upon request.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Example 1

Limitations in the related art—the major limitation in all existing distributed memory database peptide search algorithms is the inflated space complexity=O(PN) where P is the number of parallel nodes and O(N) is the space complexity of their shared-memory counter parts. The space complexity inflation stems from the replication of massive model-spectra databases at all parallel instances. Consequently, the application of existing algorithms is limited to the use cases where the indexed model-spectra database size must fit within the main memory on all system nodes to avoid the expensive memory swaps, page faults, load imbalance and out-of-core processing overheads leading to an extremely inefficient solution. Furthermore, as the PTMs are added, this memory upper-bound is quickly exhausted due to the combinatorial increase in the database size, incurring further slowdowns. For a reference, the model-spectra database constructed from a standard *Homo sapiens* proteome sequence database can grow from 3.8 million to 500 million model-spectra (0.6 TB) if only the six most common PTMs (i.e. oxidation, phosphorylation, deamidation, acetylation, methylation and hydroxylation) are incorporated. There have been some efforts towards investigations of parallel strategies that involve splitting of model-spectra databases among parallel processing units. In these designs, the database search is implemented in a stream fashion where each parallel process receives a batch of experimental data, executes partial search, and passes on the results to the next process in the stream. However, these models suffer from significant amounts of on-the-fly computations and frequent data communication between parallel nodes leading to high compute times, and limited (~50%) parallel efficiency (see, e.g., Gaurav Kulkarni, et al., A scalable parallel approach for peptide identification from large-scale mass spectrometry data, In 2009 International Conference on Parallel Processing Workshops, pages 423-430, IEEE, 2009; which is hereby incorporated by reference herein in its entirety).

Example 2

Mod Distance. The proposed Mod Distance (Δm) is used as a supplementary metric in peptide database clustering in superstep 1 (the improved LBE method). The application of this metric can be best understood through an example. Consider three database peptide sequences p: MEGSYIRK, q: ME*GSYI*RK and r: MEGS*Y*IRK. The bold letters represent the normal amino acids in the peptide and the letters followed by (*) represent the modified amino acids. In this example the Edit Distance between the pairs (Δe(p, q)=Δe(p, r)=2) cannot differentiate. Now apply the Mod Distance on this scenario which considers the shared peaks between the peptide pairs to further separate them. For example, the shared (b- and y-) ions (or peaks) between p and q are: ME*GSYI*RK=3 (underlined letters), yielding Δm(p, q)=1.625 and the peaks shared between p and r are: MEGS*Y*IRK=6 (underlined letters), yielding Δm(p, r)=1.25. This indicates that the entries p and r should be located at relatively nearby database indices. The Mod Distance can be easily generalized for other ion-series such as: a-, c-, x-, z-ions and immonium ions as well.

Example 3

Correctness of LBE. Assume the peptide precursor m/z distribution of any given database is g(m) and that of any given dataset is f(m), then the LBE algorithm statically results in fairly balanced workloads at all parallel nodes.

Proof. The algorithmic workload w(f, g) for database peptide search can be given as the cost of performing the total number of comparisons to search the dataset f(m) against the database g(m) using filter size δM and shared peaks≥k, mathematically:

$$\omega(f, g) = \text{cost}\left(\sum_{m=0}^{\infty} f(m) \sum_{z=-\delta M}^{\delta M} \text{shp}(f(m), g(m+z), k)\right)$$

where:

$\text{shp}(f,g,k) = \text{count}(\text{shared\_peaks}(f,g) \geq k)$

The above equations imply that the database distribution i.e. Σshp(f(m), g(m+z), k) must be similar at all parallel nodes in order to achieve system-wide load balance. The LBE algorithm achieves this by localizing (e.g., by δM and shared peaks) the database entries and then finely scattering them across parallel nodes (FIG. 8) producing identical local database distributions gloc(m) at parallel nodes thereby, and identical workloads. This theorem can also be extended to incorporate sequence-tag based filtration methods in a straightforward manner.

Example 4

Task Mapping. The parallel HiCOPS tasks are configured and deployed on system nodes based on the available resources, user parameters and the database size. The presented algorithm assumes a Linux based homogeneous multicore nodes cluster where the interconnected nodes have multicores, local shared memory and optionally a local storage as well. This is the most common architecture in modern supercomputers including XSEDE Comet, NERSC Cori, etc. However, alternative algorithms, operating systems, configurations, and implementations are contemplated. The resource information is read using Linux's lscpu utility. Specifically, the information about shared memory per node (λ), NUMA nodes per node (u), cores per NUMA node (cu), number of sockets per node (s) and cores per socket (cs) is read. The total size of database (D) is then estimated using protein sequence database and user parameters. Assuming the total number of system nodes to be P, the parameters: number of MPI tasks per node (tn) and the number of parallel cores per MPI task (tc) and MPI task binding level (tbl) are optimized as depicted in Algorithm 5. The optimizations ensure that: 1) System resources are efficiently utilized 2) The MPI tasks have sufficient resources to process the database and 3) The MPI tasks have an exclusive access to a disjoint partition of local compute and memory resources.

In accordance with the subject invention, in Algorithm 5, the lines 8 to 14 iteratively reduce the cores per MPI task while increasing the number of MPI tasks until the database size per MPI task is less than 48 million (empirically set for XSEDE Comet nodes). This was done to reduce the memory contention per MPI process for superior performance. The while loop may be removed or modified depending on the database search algorithms and machine parameters. The value of "48 million spectra" was set in this embodiment specific to the Comet machine, and the value may be different for other machines. The justification to select 48 million was that each socket in Comet has direct access to 64 GB RAM which can fit roughly at most 48 million spectra without having to indirectly access more than 64 GB RAM. This number may need to be set for each individual system by the user, based on available system resources and database parameters.

Exemplary Algorithms

The following algorithms can be used with embodiments of the subject invention.

---

Algorithm 1
Algorithm 1: Partial Database Construction in Superstep 1

Data: peptide sequences ($\epsilon$)
Results: indexed partial Database ($D_i$)
   /* generate databse entries            */
1  for s in $\epsilon$ do in parallel
2  | for v in $2^m$ do
3  | | e ← gen_entry(v);
   | | /* add to partial database if mine  */
4  | | if is_mine($e_v$) then
5  | | | E.append(e);
   | |
   |
   /* generate model-spectra               */
6  for s in $D_i$ do in parallel
7  | S.append(model_spectrum(s));
   /* index the database in parallel       */
8  $D_i$ ← map(parallel_sort(E), parallel_index(S));
   /* return the indexed parital database  */
9  return $D_i$;

---

Algorithm 2
Algorithm 2: Data load (per thread) by sub-task R (Superstep 3)

Data: forward queue ($q_f$), recycle queue ($q_r$), pointer stack ($s_d$), batch index ($i_d$)
   /* loop unless $q_f$ full, preempted or no more batches */
1  while ~ $q_f$.full ( ) do
   | /* check pointer stack                */
2  | if ~ dp then
3  | | dp ← $s_d$.pop( );
   | /* if stack is empty, get a new pointer */
4  | if ~ dp then
5  | | dp ← $i_d$.pop( );
   | /* no more experimental data batches - exit */
6  | if ~ dp then
7  | | break;
   | /* check preemption state at $q_r$ status */
8  | if ~ preempt ( ) or ~ $q_r$.empty ( ) then
9  | | $s_d$.push(dp);
10 | | break;
11 | else
   | | /* else get a buffer from $q_r$.    */
12 | | bp ← $q_r$.pop ( );
   | /* read a batch of expt data          */
13 | dp.read_batch(bp);
   | /* push the buffer to $q_f$           */
14 | $q_f$.push(bp);

---

Algorithm 3
Algorithm 3: Partial DB search by sub-task R (Superstep 3)

Data: forward queue ($q_f$), recyle queue ($q_r$), partial database ($D_{p_i}$), result queue ($q_k$)
   /* extract a batch from queue           */
1  b ← $q_f$.pop( );
   /* data parallel search                 */
2  for e in b do in parallel
   | /* apply the precursor mass filter    */
3  | $\sigma_{p_i}$ ← filter$_1$($D_{p_i}$, e);
4  | if $\sigma_{p_i}$ then
5  | | for β in e do
   | | | /* apply the shared peaks filter  */
6  | | | $\mu_{p_i}$.append(filter$_2$($\sigma_{p_i}$,β));
   | | | /* score against the filtered database */
7  | | | for h in $\mu_{p_i}$ do
8  | | | | heap.push(k ← score(h,e));
   | | | /* append to a batch of intermediate results */

---

Algorithm 3
Algorithm 3: Partial DB search by sub-task R (Superstep 3)

9  | | | res$_i$.append(heap);
   |
   /* recycle the buffer back to $q_r$    */
10 $q_r$.push(b);
   /* push the intermediate results batch to $q_k$ */
11 $q_k$.push(res$_i$);

---

Algorithm 4
Algorithm 4: Result Assembly in Superstep 4

Data: rank $p_i$, Intermediate Result batches ($r_i$)
Result: expect scores (ev)
   /* extract a batch from queue           */
1  b ← $q_f$.pop( );
   /* get batches that satisfy the condition */
2  for b in (b mod $p_i$ = 0) do
3  | l.append(b);
   /* data parallel assembling of results for each batch */
4  for s in l do in parallel
   | /* assemble the null distribution     */
5  | dist ← assemble(s);
   | /* max heapify the scores             */
6  | heap ← make_heaps(s);
   | /* use either fitting method          */
7  | fit ← logWeibullFit(dist);
8  | fit ← TailFit(dist);
   | /* get the top hit from heap          */
9  | $g_{max}$ ← heap.pop( ).value( );
   | /* compute the expect score           */
10 | ev ← (fit.w × $g_{max}$ + fit.b) × heap.size( );
   | /* push results to a map structure    */
11 | map.push(key = $g_{max}$.key( ), val = ev);
   /* asynchronous scatter complete result data */
12 for $p_i$ in P do in parallel
13 | isend(map.data(key = $p_i$), dest = $p_i$);
   /* synchronize using barrier            */
14 barrier( );
   /* write the results to the file system */
15 write(map.data(key = rank));

---

Algorithm 5
Algorithm 5: Task Mapping

Data: number of nodes (n), node parameters ($\lambda$, u, $c_u$, s, $c_s$) and database size (D)
Result: number of MPI tasks per node ($t_n$), cores per MPI task ($t_c$) and MPI binding level ($t_{bl}$)
   /* ensure enough memory for database    */
1  if $D_{p_i}$ ← D/P > 0.70$\lambda$ then
2  | return err;
   /* set MPI binding level                */
3  $t_{bl}$ ← max{u, c};
   /* set MPI binding policy               */
4  $t_{bp}$ ← scatter;
   /* set cores per MPI task               */
5  $t_c$ ← min {$c_u$, $c_s$};
   /* set number of MPI task per node      */
6  $t_n$ ← max{u, c};
7  $t_{max}$ ← $t_c$;
   /* Optional: optimize for memory bandwidth */
8  while (D/$t_n$ > 48 × $10^6$) do
   | /* Choose the next highest factor of $t_{max}$ */
9  | $n_{poss}$ ← factorize($t_{max}$);
10 | if $n_{poss}$ ≥ $t_{max}$/2 then
11 | | $t_n$ ← $t_n$ × $t_{max}$/$n_{poss}$;
12 | | $t_c$ ← $n_{poss}$;
13 | else
14 | | break;
   |
15 return $t_n$, $t_c$, $t_{bl}$, $t_{bp}$;

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for rapid and efficient peptide identification from large-scale mass spectrometry data through high performance computing database peptide search, the system comprising:
   a symmetric multiprocessor supercomputer comprising a plurality of processors and shared resources, the shared resources comprising a shared memory storage in operable communication with the plurality of processors; and
   at least one machine-readable medium in operable communication with the plurality of processors, the at least one machine-readable medium having instructions stored thereon that, when executed by one or more processors of the plurality of processors, perform the following supersteps:
   (a) extracting, by the one or more processors, a plurality of peptide database partitions (PDBs) from a peptide database and then indexing the plurality of PDBs, the plurality of PDBs being extracted by clustering data entries of the peptide database based at least on a Mod Distance (μm) metric and load balancing the clustered data entries evenly across the PDBs;
   (b) providing, by the one or more processors, a plurality of experimental spectra, each spectrum of the plurality of experimental spectra comprising a batch of pre-processed mass spectrometry data from a mass spectrometry data set of a database;
   (c) completing, by the one or more processors, a peptide search of the plurality of experimental spectra against the plurality of PDBs to produce a plurality of partial results and serializing the plurality of partial results; and
   (d) assembling, de-serializing, and synchronizing the plurality of partial results to form a complete result for identifying peptides, and writing the complete result to a file system, thus providing the rapid and efficient peptide identification from large-scale mass spectrometry data,
the peptide search further comprising the following steps:
   (i) loading the plurality of experimental spectra into a plurality of forward queues (qf) in the shared memory storage;
   (ii) reading the plurality of experimental spectra from each respective forward queue in the plurality of forward queues, recycling the forward queue as a return queue (qr), searching the spectra against the plurality of PDBs to produce the plurality of partial results, and writing the plurality of partial results to a plurality of intermediate queues (qk) in the shared memory storage; and
   (iii) reading the partial results from each respective intermediate queue in the plurality of intermediate queues, recycling each intermediate queue as an intermediate return queue (qk'), serializing the plurality of partial results, and writing the plurality of partial results to the shared memory storage.

2. The system according to claim 1, the Mod Distance (Δm) given as:

$$\Delta m(x, y) = 2 - \frac{a}{\max(len(x), len(y))}$$

for a pair of peptide database entries (x, y), where the sum of unedited letters from both sequence termini is (a).

3. The system according to claim 2, at least one processor of the plurality of processors having a main memory locally connected thereto, and each spectrum of the plurality of experimental spectra provided in superstep (b) having a size selected to fit within the main memory.

4. The system according to claim 1, the superstep (c) comprising actively allocating shared resources across steps (i), (ii), and (iii) to optimize performance in a multi-threaded, multi-core, shared memory, parallel process, producer-consumer pipeline.

5. The system according to claim 4, the system comprising measurable performance parameters, the performance parameters comprising one or more of: shared memory per node ($\lambda$); NUMA nodes per node (u); cores per NUMA node (cu); number of sockets per node (s); cores per socket (cs); estimated or actual total size of database (D); total number of system nodes (P); number of MPI tasks per node (tn); number of parallel cores per MPI task (tc); and MPI task binding level (tbl).

6. The system according to claim 5, the superstep (c) comprising determining allocation of shared resources based on one or more of the performance parameters.

7. The system according to claim 1, the superstep (d) comprising a first parallel sub-task comprising de-serialization and assembly of the plurality of partial results, and a second parallel sub-task comprising data smoothing and application of a significance test to compute e-Values.

8. The system according to claim 5, the symmetric multiprocessor supercomputer comprising processing cores allocated to MPI tasks, and
   the instructions when executed by one or more processor of the plurality of processors further performing a step of iteratively reducing the number of parallel cores per MPI task while increasing the number of MPI tasks until the PDB size per MPI task reaches a defined threshold.

9. A method for rapid and efficient peptide identification from large-scale mass spectrometry data through high performance computing database peptide search, the method comprising:
   providing a symmetric multiprocessor supercomputer comprising a plurality of processors and shared resources, the shared resources comprising a shared memory storage in operable communication with the plurality of processors, and at least one machine-readable medium in operable communication with the plurality of processors; and
   performing the following supersteps:
   (a) extracting, by at least one processor of the plurality of processors, a plurality of peptide database partitions (PDBs) from a peptide database and then indexing the plurality of PDBs, the plurality of PDBs being extracted by clustering data entries of the peptide database based at least on a Mod Distance (Δm) metric and load balancing the clustered data entries evenly across the PDBs;

(b) providing, by at least one processor of the plurality of processors, a plurality of experimental spectra, each spectrum of the plurality of experimental spectra comprising a batch of pre-processed mass spectrometry data from a mass spectrometry data set of a database;

(c) completing, by at least one processor of the plurality of processors, a peptide search of the plurality of spectra against the plurality of PDBs to produce a plurality of partial results and serializing the plurality of partial results; and (d) assembling, de-serializing, and synchronizing, by at least one processor of the plurality of processors, the plurality of partial results to form a complete result for identifying peptides, and writing the complete result to a file system, thus providing the rapid and efficient peptide identification from large-scale mass spectrometry data, the peptide search further comprising the following steps:
(i) loading the plurality of spectra into a plurality of forward queues (qf) in the shared memory storage;
(ii) reading the spectra from each respective forward queue in the plurality of forward queues, recycling the forward queue as a return queue (qr), searching the spectra against the plurality of PDBs to produce the plurality of partial results, and writing the plurality of partial results to a plurality of intermediate queues (qk) in the shared memory storage; and
(iii) reading the partial results from each respective intermediate queue in the plurality of intermediate queues, recycling each intermediate queue as an intermediate return queue (qk'), serializing the plurality of partial results, and writing the plurality of partial results to the shared memory storage.

10. The method according to claim 9, the Mod Distance ($\Delta m$) is given as:

$$\Delta m(x, y) = 2 - \frac{a}{\max(len(x), len(y))}$$

for a pair of peptide database entries (x, y), where the sum of unedited letters from both sequence termini is (a).

11. The method according to claim 10, each processor of the plurality of processors having a main memory locally connected thereto, and each spectrum of the plurality of experimental spectra provided in superstep (b) having a size selected to fit within the main memory.

12. The method according to claim 9, the superstep (c) comprising actively allocating shared resources across steps (i), (ii), and (iii) to optimize performance in a multi-threaded, multi-core, shared memory, parallel process, producer-consumer pipeline.

13. The method according to claim 12, the system comprising measurable performance parameters, the performance parameters comprising one or more of: shared memory per node ($\lambda$); NUMA nodes per node (u); cores per NUMA node (cu); number of sockets per node (s); cores per socket (cs); estimated or actual total size of database (D); total number of system nodes (P); number of MPI tasks per node (tn); number of parallel cores per MPI task (tc); and MPI task binding level (tbl), and superstep (c) comprising determining allocation of shared resources based on one or more of the performance parameters.

14. The method according to claim 13, the superstep (d) comprising a first parallel sub-task comprising de-serialization and assembly of the plurality of partial results, and a second parallel sub-task comprising data smoothing and application of a significance test to compute e-Values.

15. A system for rapid and efficient peptide identification from large-scale mass spectrometry data through high performance computing database peptide search, the system comprising:

a symmetric multiprocessor supercomputer comprising a plurality of processors and shared resources, the shared resources comprising a shared memory storage in operable communication with the plurality of processors; and at least one machine-readable medium in operable communication with the plurality of processors, the at least one machine-readable medium having instructions stored thereon that, when executed by one or more processors of the plurality of processors, perform the following supersteps:

(a) providing, by the one or more processors, a plurality of peptide database partitions (PDBs) from a peptide database and then indexing the plurality of PDBs, the plurality of PDBs being extracted by clustering data entries of the peptide database based at least on a Mod Distance ($\Delta m$) metric and load balancing the clustered data entries evenly across the PDBs;

(b) providing, by the one or mare processors, a plurality of experimental spectra, each spectrum of the plurality of experimental spectra comprising a batch of pre-processed mass spectrometry data from a mass spectrometry data set of a database;

(c) completing a peptide search of the plurality of experimental spectra against the plurality of PDBs to produce a plurality of partial results and serializing the plurality of partial results; and (d) assembling, de-serializing, and synchronizing the plurality of partial results to form a complete result for identifying peptides, and writing the complete result to a file system, thus providing the rapid and efficient peptide identification from large-scale mass spectrometry data;

the superstep (a) comprising peptide database clustering based on the Mod Distance ($\lambda m$), given as:

$$\Delta m(x, y) = 2 - \frac{a}{\max(len(x), len(y))}$$

for a pair of peptide database entries (x, y), where the sum of unedited letters from both sequence termini is (a), each of the plurality of processors having a main memory locally connected, and each of the plurality of experimental spectra provided in superstep (b) having a size selected to fit within the main memory on one of the plurality of processors, the partial database peptide search comprising the following steps:
(i) loading the plurality of experimental spectra into a plurality of forward queues (qf) in the shared memory storage;
(ii) reading the plurality of experimental spectra from each respective forward queue in the plurality of forward queues, recycling the forward queue as a return queue (qr), searching the spectra against the plurality of PDBs to produce the plurality of partial results, and writing the plurality of partial results to a plurality of intermediate queues (qk) in the shared memory storage; and (iii) reading the partial results from each respective intermediate queue in the plurality of intermediate queues, recycling each intermediate queue as an intermediate return queue (qk'), serializing the plurality of partial results and writing the plurality of partial results to the shared memory storage, and the superstep (c) comprising actively allocating shared resources across steps (i), (ii), and (iii) to optimize performance in a multi-threaded, multi-core, shared memory, parallel process, producer-consumer pipeline.

16. The system according to claim 15, the system comprising measurable performance parameters, the performance parameters comprising one or more of: shared memory per node ($\lambda$); NUMA nodes per node (u); cores per NUMA node (cu); number of sockets per node (s); cores per socket (cs); estimated or actual total size of database (D); total number of system nodes (P); number of MPI tasks per node (tn); number of parallel cores per MPI task (tc); and MPI task binding level (tbl), superstep (c) comprising determining allocation of shared resources based on one or more of the performance parameters, the superstep (d) comprising a first parallel sub-task comprising de-serialization and assembly of the plurality of partial results, and a second parallel sub-task comprising data smoothing and application of a significance test to compute e-Values, the symmetric multiprocessor supercomputer comprising processing cores allocated to MPI tasks, the system comprising a step of iteratively reducing the number of parallel cores per MPI task while increasing the number of MPI tasks until the PDB size per MPI task reaches a defined threshold, and the threshold being chosen to optimize system performance of the symmetric multiprocessor supercomputer.

\* \* \* \* \*